(12) United States Patent
Ad

(10) Patent No.: US 10,631,868 B2
(45) Date of Patent: Apr. 28, 2020

(54) SYSTEM FOR OCCLUSION OF LEFT ATRIAL APPENDAGE

(71) Applicant: Niv Ad, North Bethesda, MD (US)

(72) Inventor: Niv Ad, North Bethesda, MD (US)

(*) Notice: Subject to any disclaimer, the term of this patent is extended or adjusted under 35 U.S.C. 154(b) by 211 days.

(21) Appl. No.: 15/681,812

(22) Filed: Aug. 21, 2017

(65) Prior Publication Data
US 2017/0340335 A1     Nov. 30, 2017

Related U.S. Application Data

(63) Continuation-in-part of application No. 14/809,473, filed on Jul. 27, 2015, now Pat. No. 9,737,309, which
(Continued)

(51) Int. Cl.
*A61B 17/12*     (2006.01)
*A61B 17/00*     (2006.01)
(Continued)

(52) U.S. Cl.
CPC .... *A61B 17/12122* (2013.01); *A61B 17/0057* (2013.01); *A61B 17/122* (2013.01);
(Continued)

(58) Field of Classification Search
CPC .......... A61B 17/0057; A61B 17/12013; A61B 17/12022; A61B 17/12031;
(Continued)

(56) References Cited

U.S. PATENT DOCUMENTS 3,538,917 A    11/1970   Selker
4,708,140 A    11/1987   Baron
(Continued)

FOREIGN PATENT DOCUMENTS

GB     1268034 A    3/1972
WO    03/096881 A2   11/2003
(Continued)

OTHER PUBLICATIONS

International Search Report and Written Opinion dated Oct. 18, 2018 for International Patent Application No. PCT-US2018-047233 filed Aug. 21, 2018, all pages.
(Continued)

*Primary Examiner* — Robert A Lynch
(74) *Attorney, Agent, or Firm* — Kilpatrick, Townsend & Stockton LLP

(57) ABSTRACT

An epicardial implant having a positioning device that defines an open interior. The positioning device is configured to be detachably coupled with an implant delivery device such that the positioning device may be detached from the implant delivery device after the implant is in place about an atrial appendage. The positioning device has first and second sides with a distal end that couples the first and second sides. The implant includes an expandable cuff coupled with the positioning device. The positioning device is configured to selectively move the expandable cuff toward and away from an atrial appendage to position the expandable cuff in a desired position relative to the atrial appendage. The expandable cuff is expandable into at least a portion of the open interior of the positioning device to physically occlude a base of the atrial appendage following placement of the expandable cuff into the desired position.

18 Claims, 23 Drawing Sheets

Related U.S. Application Data is a continuation of application No. 13/168,009, filed on Jun. 24, 2011, now abandoned.

(60) Provisional application No. 61/358,127, filed on Jun. 24, 2010.

(51) Int. Cl.
*A61B 17/34* (2006.01)
*A61B 17/122* (2006.01)
*A61B 17/128* (2006.01)
*A61B 17/22* (2006.01)
*A61B 17/30* (2006.01)

(52) U.S. Cl.
CPC .... *A61B 17/12013* (2013.01); *A61B 17/1285* (2013.01); *A61B 17/3468* (2013.01); *A61B 2017/0046* (2013.01); *A61B 2017/00243* (2013.01); *A61B 2017/00557* (2013.01); *A61B 2017/00566* (2013.01); *A61B 2017/22051* (2013.01); *A61B 2017/306* (2013.01)

(58) Field of Classification Search
CPC .......... A61B 17/1204; A61B 17/12099; A61B 17/12122; A61B 17/12136; A61B 17/1285; A61B 2017/00243; A61B 2017/00557
See application file for complete search history.

(56) References Cited

U.S. PATENT DOCUMENTS

| | | | |
|---|---|---|---|
| 4,800,879 A | 1/1989 | Golyakhovsky et al. | |
| 5,306,234 A | 4/1994 | Johnson | |
| 5,624,454 A | 4/1997 | Palti et al. | |
| 6,036,706 A * | 3/2000 | Morejohn | A61B 17/122 606/157 |
| 6,146,394 A | 11/2000 | Morejohn et al. | |
| 6,290,674 B1 | 9/2001 | Roue et al. | |
| 6,458,100 B2 | 10/2002 | Roue et al. | |
| 6,488,689 B1 | 12/2002 | Kaplan et al. | |
| 6,561,969 B2 | 5/2003 | Frazier et al. | |
| 6,746,472 B2 | 6/2004 | Frazier et al. | |
| 7,011,682 B2 | 3/2006 | Lashinski et al. | |
| 7,115,110 B2 | 10/2006 | Frazier et al. | |
| 7,128,073 B1 | 10/2006 | Van der Burg et al. | |
| 7,152,605 B2 | 12/2006 | Khairkhahan et al. | |
| 7,226,458 B2 | 6/2007 | Kaplan et al. | |
| 7,318,829 B2 | 1/2008 | Kaplan et al. | |
| 7,344,543 B2 | 3/2008 | Sra | |
| 7,419,498 B2 | 9/2008 | Opolski et al. | |
| 7,549,983 B2 | 6/2009 | Roue et al. | |
| 7,566,336 B2 | 7/2009 | Corcoran et al. | |
| 7,591,818 B2 | 9/2009 | Bertolero et al. | |
| 7,597,704 B2 | 10/2009 | Frazier et al. | |
| 7,634,319 B2 | 12/2009 | Schneider et al. | |
| 7,645,285 B2 | 1/2010 | Cosgrove et al. | |
| 9,737,309 B1 | 8/2017 | Ad | |
| 2002/0049457 A1 | 4/2002 | Kaplan et al. | |
| 2002/0072759 A1 | 6/2002 | Fry | |
| 2003/0199923 A1 | 10/2003 | Khairkhahan et al. | |
| 2003/0225443 A1 | 12/2003 | Kiran et al. | |
| 2004/0044361 A1 | 3/2004 | Frazier et al. | |
| 2004/0230222 A1 | 11/2004 | Van der Burg et al. | |
| 2005/0033287 A1 | 2/2005 | Sra | |
| 2005/0149069 A1 | 7/2005 | Bertolero et al. | |
| 2005/0177182 A1 | 8/2005 | Van der Burg et al. | |
| 2005/0192531 A1 | 9/2005 | Birk | |
| 2006/0167444 A1 | 7/2006 | Swanson | |
| 2006/0206148 A1 | 9/2006 | Khairkhahan et al. | |
| 2006/0253129 A1 | 11/2006 | Liddicoat et al. | |
| 2007/0016228 A1 | 1/2007 | Salas | |
| 2007/0021761 A1 | 1/2007 | Phillips | |
| 2007/0043344 A1 | 2/2007 | McAuley | |
| 2007/0073313 A1 | 3/2007 | Liddicoat et al. | |
| 2007/0250086 A1 | 10/2007 | Wiley et al. | |
| 2008/0033457 A1 | 2/2008 | Francischelli et al. | |
| 2008/0039879 A1 | 2/2008 | Chin et al. | |
| 2008/0269788 A1 | 10/2008 | Phillips | |
| 2009/0163846 A1 | 6/2009 | Aklog et al. | |
| 2009/0240269 A1 | 9/2009 | Denis | |
| 2010/0145361 A1 | 6/2010 | Francischelli et al. | |
| 2011/0009853 A1 | 1/2011 | Bertolero et al. | |
| 2014/0364901 A1 | 12/2014 | Kiser et al. | |
| 2017/0042550 A1 | 2/2017 | Chakraborty et al. | |
| 2017/0196568 A1 | 7/2017 | Gross et al. | |

FOREIGN PATENT DOCUMENTS

| | | |
|---|---|---|
| WO | 2009/106907 A1 | 9/2009 |
| WO | 2014-190317 A2 | 11/2014 |

OTHER PUBLICATIONS

Non-Final Office Action dated Jul. 9, 2019 in U.S. Appl. No. 15/661,580, all pages.

* cited by examiner

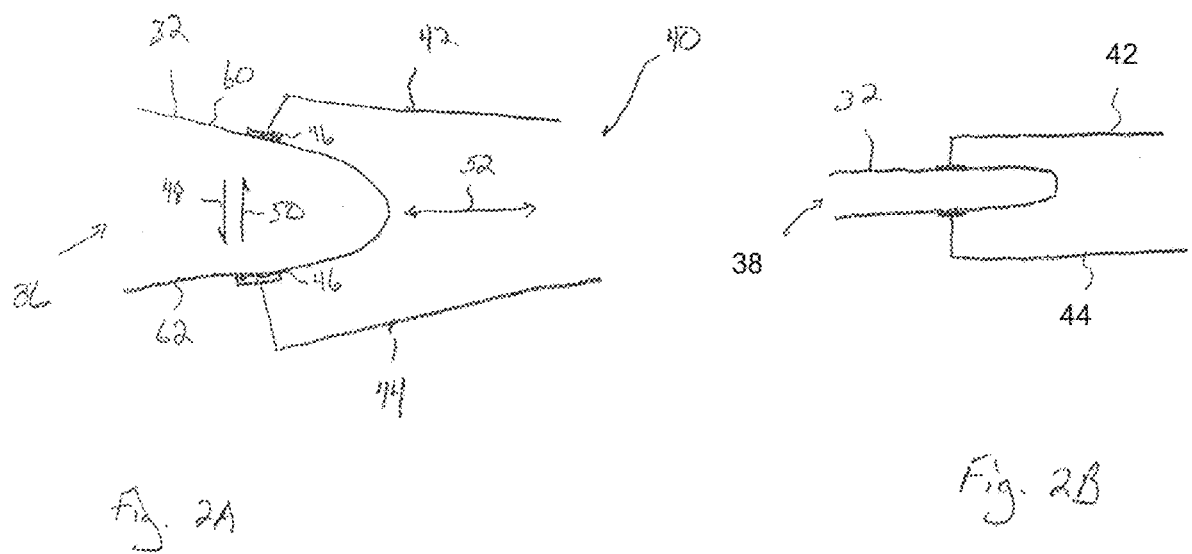

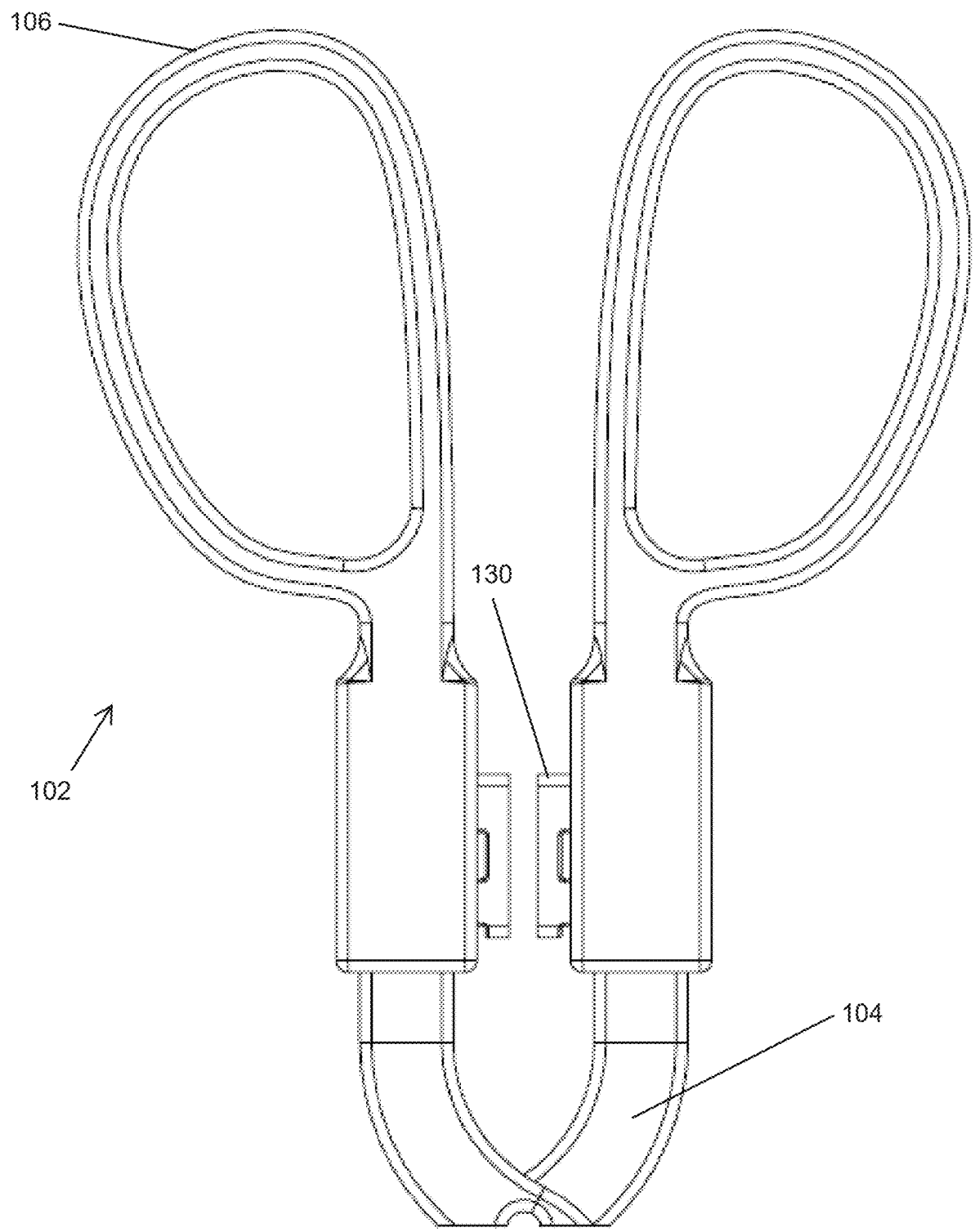

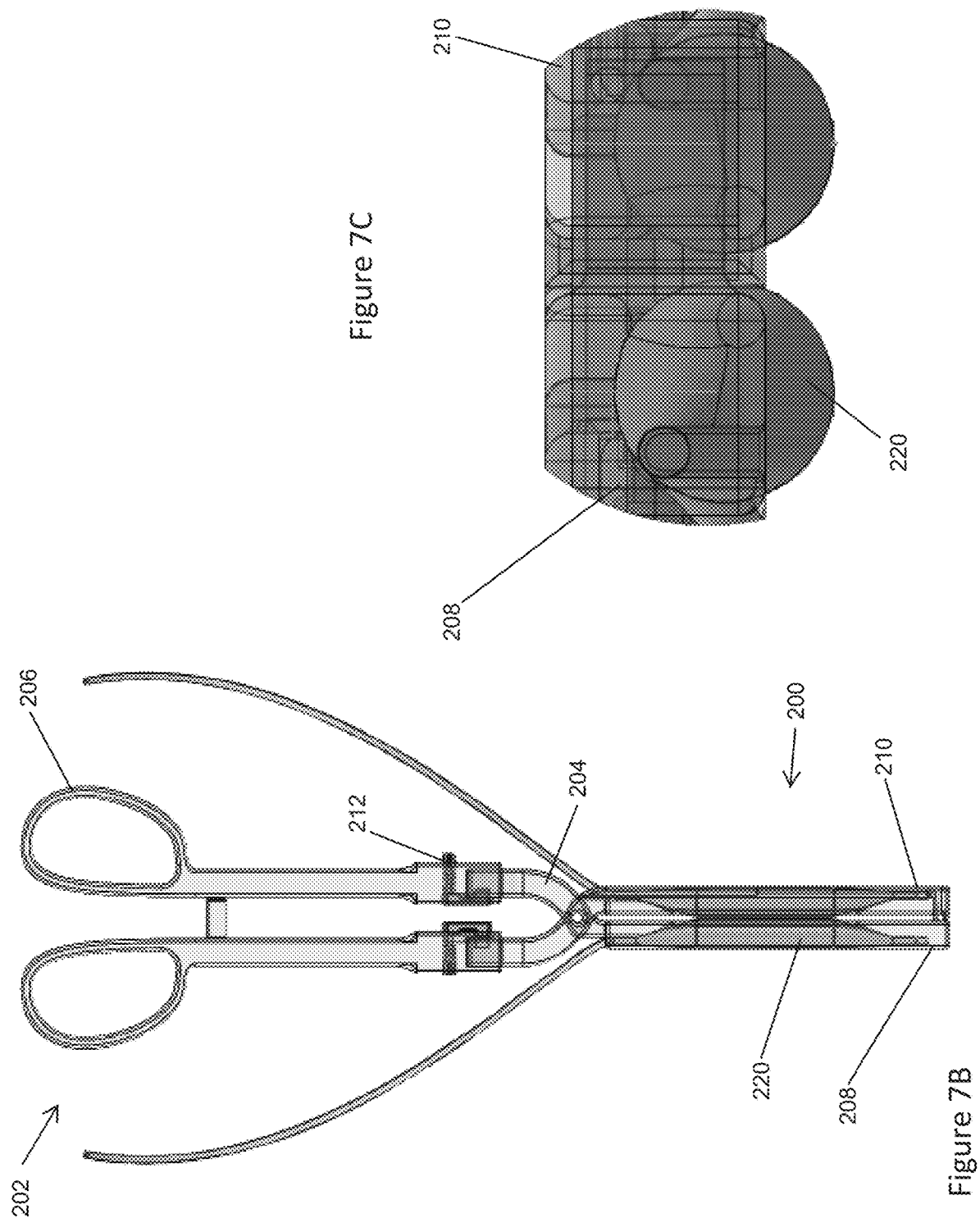

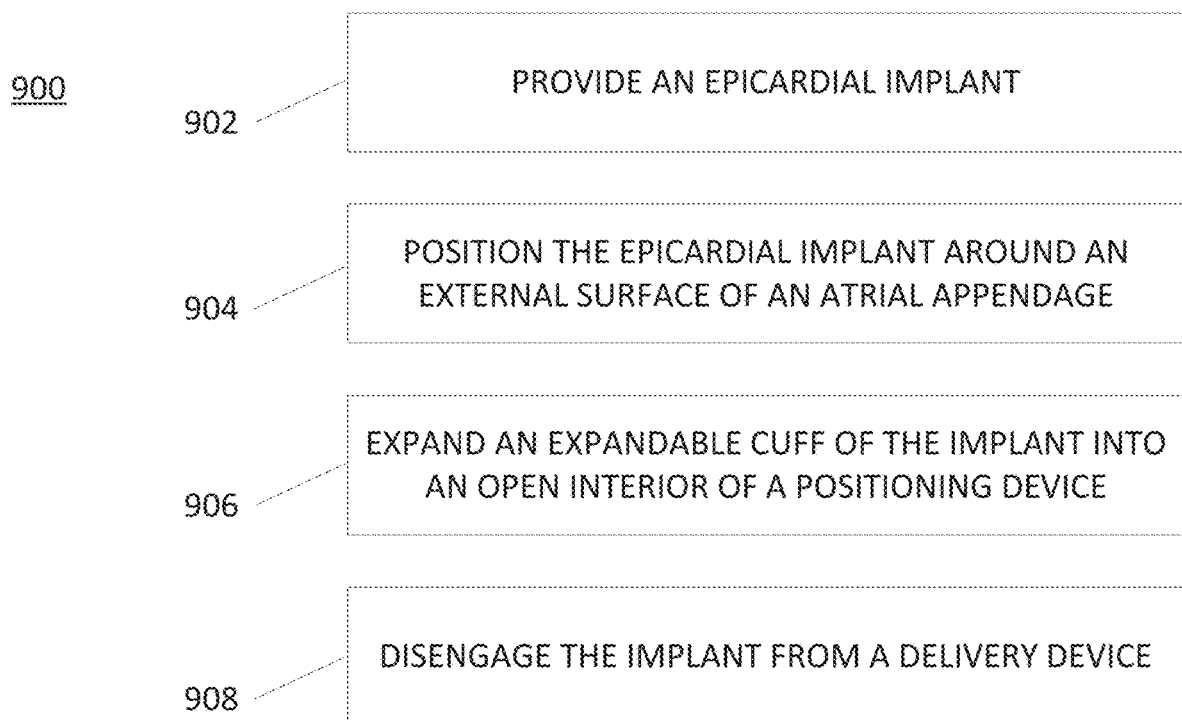

SYSTEM FOR OCCLUSION OF LEFT ATRIAL APPENDAGE

CROSS-REFERENCES TO RELATED APPLICATIONS

This application is a continuation-in-part of U.S. Pat. No. 9,737,309, filed on Jul. 27, 2015, which is a continuation of U.S. patent application Ser. No. 13/168,009, filed on Jun. 24, 2011 and entitled "System for Occlusion of Left Atrial Appendage", which itself claims priority to U.S. provisional Patent Application Ser. No. 61/358,127, filed on Jun. 24, 2010 and entitled "System for Occlusion of Left Atrial Appendage", the contents of which being incorporated herein in their entirety.

BACKGROUND OF THE INVENTION

Atrial fibrillation ("AF") is a common cardiac rhythm disorder ("cardiac arrhythmia") and is characterized by a rapid chaotic heartbeat in which the upper chambers of the heart known as the atria quiver rapidly instead of beating in a steady rhythm. This rapid quivering reduces the heart's ability to properly function as a pump.

Atrial fibrillation typically increases the risks of thromboembolic stroke and congestive heart failure. Quality of life is also impaired by common AF symptoms such as palpitations, chest pain, fatigue, and dizziness. The irregular heartbeat associated with AF causes blood to pool in the left atrial appendage, allowing clots to accumulate over time. From time to time, clots may dislodge from the left atrial appendage, and may enter various circulation tracks causing strokes, myocardial infarction, limb ischemia, and other vascular problems.

A number of approaches have been implemented to address the health risks associated with AF. Among such techniques, surgical procedures for closing (occluding) the left atrial appendage (LAA) have been proposed. Some of such procedures involve open chest wall midsternotomy procedures while others may access the pericardial space through a thoracotomy or from a sub-xiphoid access point. In such approaches, a physical device is typically employed to cinch or compress the LAA.

Conventional LAA closure devices, however, are difficult to precisely position at the LAA, and therefore result in incomplete occlusion of the LAA, as the surgical closure point is oftentimes spaced from the base of the LAA. Moreover, conventional closure devices lack simple repositioning and adjustment capabilities, such that attempts to physiologically completely occlude the LAA frequently fail.

It is therefore an object of the invention to provide a tissue occlusion device which facilitates placement and ultimate closure of the left atrial appendage at its base.

It is another object of the present invention to provide an atrial appendage closure device having adjustment capabilities to facilitate re-positioning of the device at the atrial appendage, and complete occlusion of the appendage at its base.

BRIEF SUMMARY OF THE INVENTION

Embodiments of the invention are directed to epicardial implants that are designed to occlude the atrial appendage. The implants described herein provide the ability to reposition the implant prior to expanding one or more expandable cuffs or balloons and are usable in open-chest and/or percutaneous applications.

In one aspect, an epicardial implant is provided. The implant may include a positioning device that defines an open interior. The positioning device may be configured to be detachably coupled with an implant delivery device such that the positioning device may be detached from the implant delivery device after the epicardial implant is in place about an atrial appendage. The positioning device may include a first side, a second side, and a distal end that couples the first side and the second side. The implant may also include at least one expandable cuff coupled with the positioning device. The positioning device may be configured to selectively move the at least one expandable cuff toward and away from an atrial appendage to position the at least one expandable cuff in a desired position relative to the atrial appendage. The at least one expandable cuff may be expandable into at least a portion of the open interior of the positioning device following placement of the at least one expandable cuff into the desired position. The at least one expandable cuff may be configured to physically occlude a base of the atrial appendage when expanded.

In another aspect, an epicardial implant may include a catheter system that has a catheter body defining at least one lumen and a positioning device disposed within the catheter body. The positioning device may define an open interior. The positioning device may be configured to extend from a distal end of the catheter body. The positioning device may be configured to be positioned such that at least portion of a base of an atrial appendage is disposed within the open interior. The implant may also include at least one expandable cuff. The positioning device may be configured to selectively move the expandable cuff toward and away from the atrial appendage to position the at least one expandable cuff in a desired position relative to the atrial appendage. The at least one expandable cuff may be expandable into at least a portion of the open interior of the positioning device following placement of the at least one expandable cuff into the desired position. The at least one expandable cuff may be configured to physically occlude a base of the atrial appendage when expanded.

In another aspect, a method for treating an atrial appendage is provided. The method may include providing an epicardial implant. The epicardial implant may include a positioning device defining an open interior. The positioning device may include a first side, a second side, and a distal end that couples the first side and the second side. The implant may also include at least one expandable cuff that is expandable into at least a portion of the open interior of the positioning device. The method may also include positioning the epicardial implant around an external surface of the atrial appendage such that a base of the atrial appendage is disposed in the open interior of the positioning device. The method may further include expanding the at least one expandable cuff into the open interior of the positioning device to an extent sufficient to physically occlude the atrial appendage at the base.

BRIEF DESCRIPTION OF THE DRAWINGS

FIG. 2A is a top schematic view of a portion of the atrial appendage occlusion device illustrated in FIGS. 1 and 2 in an open condition;

FIG. 2B is a top schematic view of a portion of the atrial appendage occlusion device illustrated in FIGS. 1 and 2 in a closed condition;

FIG. 6K depicts a top cross-sectional view of a quick release mechanism of the epicardial implant system of FIG. 6A according to embodiments.

FIG. 7B depicts a top view of the epicardial implant system of FIG. 7A in an open state according to embodiments.

FIG. 7C depicts a front cross-sectional view of a positioning device of the epicardial implant system of FIG. 7A according to embodiments.

FIG. 9 is a flowchart depicting a process of occluding an atrial appendage according to embodiments.

DETAILED DESCRIPTION OF THE INVENTION

Figure 1:
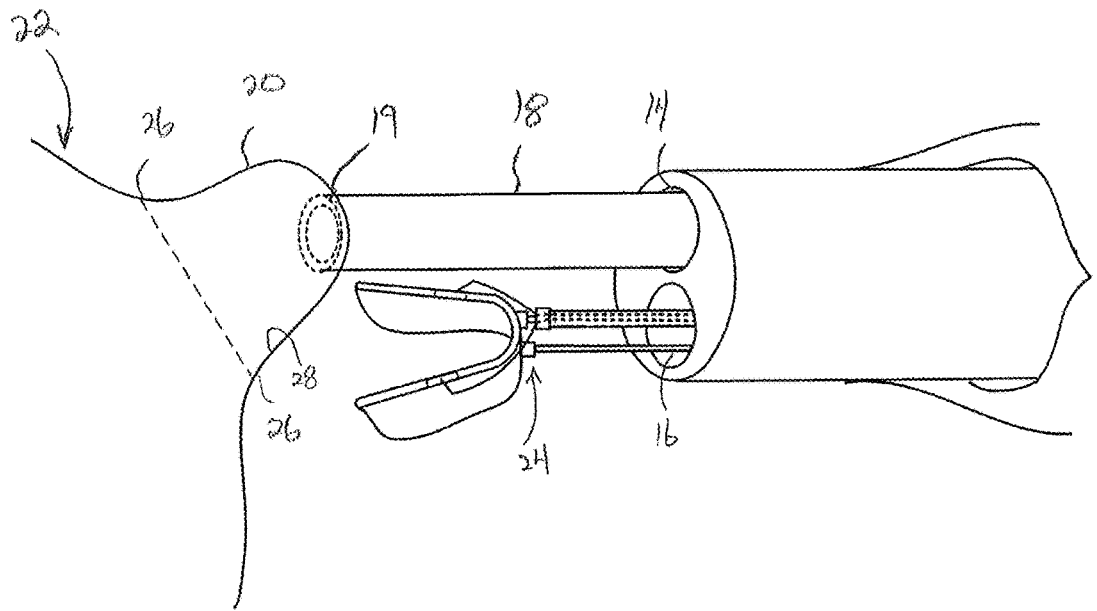
FIG. 1 is a schematic diagram of an atrial appendage occlusion device of the present invention.

The objects and advantages enumerated above together with other objects, features, and advances represented by the present invention will now be presented in terms of detailed embodiments described with reference to the attached drawing figures which are intended to be representative of various embodiments of the invention. Other embodiments and aspects of the invention are recognized as being within the grasp of those having ordinary skill in the art.

Embodiments of the invention provide epicardial implants that are usable to physically occlude an atrial appendage in the treatment of atrial fibrillation. The implants described herein may be usable in percutaneous procedures and/or open-chest procedures. Delivery devices may be used to position epicardial implants around an atrial appendage. For example, in percutaneous applications, a catheter delivery system may be used, while in some open-chest applications, a forceps-like delivery system may be used. Each epicardial implant, or atrial appendage occlusion device, may include a positioning device, or clamp, that defines an open interior between at least two sides and one or both of a proximal and distal end. The positioning device may be configured to selectively move one or more expandable cuffs toward and away from an atrial appendage to position the expandable cuff(s) in a desired position relative to the atrial appendage. The positioning device may be configured to be detachably coupled with an implant delivery device such that the positioning device may be detached from the implant delivery device after the epicardial implant is in place about an atrial appendage. The positioning device may include a first side, a second side, and a distal end that couples the first side and the second side.

For example, in some open-chest applications, the positioning device may include two side prongs that are movably coupled with one another via a hinge. The prongs may be positioned around a base of an atrial appendage and closed such that the prongs largely come together, oftentimes to a generally parallel (within 5° of parallel) state. A distal end of the prongs may include a clasp or latch that may be used to close and secure the two prongs together.

In percutaneous applications, the positioning device may include a support wire that forms a loop or hook which has a first side, a second side, and at least one end that together define an open interior of the positioning device. The open interior of the support wire is expandable for positioning about the base of the atrial appendage. The positioning device may also include a shape memory wire. To position the epicardial implant around an external surface of the atrial appendage, the support wire may be manipulated (using a guide wire) to a position in which an outer periphery of the support wire encircles at least a portion of the base of the atrial appendage. The support wire may then be removed, enabling the shape memory wire to rebound to a preset shape that is configured to close the open interior of the positioning device around the base of the atrial appendage.

As discussed above, the implant may also include one or more expandable cuffs that are each coupled with the positioning device. In some embodiments, the expandable cuff is a balloon that is inflatable by introducing a fluid into an interior of the balloon. The expandable cuff may be expandable into at least a portion of the open interior of the positioning device following placement of the expandable cuff into the desired position. The expandable cuff may be configured to physically occlude a base of the atrial appendage when expanded.

With reference now to the drawings, and first to FIG. 1, an atrial appendage occlusion device 10 includes a multiple lumen delivery device 12, such as a steerable catheter, as is well known in the art. In one embodiment, delivery device 12 includes first and second lumens 14, 16 for simultaneously delivering a plurality of devices to, for example, the left atrial appendage (LAA) 20 of a left atrium 22 of a human heart. In the illustrated embodiment, a grasping device 18 may be delivered through first lumen 14, while an implant 24 may be delivered through second lumen 16 of delivery device 12.

One aspect of the present invention provides for laparoscopic/percutaneous transport of delivery device 12 to LAA 20. In some embodiments, delivery device 12 is a distally steerable catheter for minimally invasive introduction to the pericardial space through the pleural or sub-xiphoid spaces using a seldinger technique. In such a manner, implant 24 of the present invention may be delivered to the LAA without the need for midsternotomy. It is to be understood, however, that the device 10 of the present invention may be useful for direct access to the LAA in cases where the patient is undergoing a midstemotomy for other surgical procedures. In either scenario, device 10 is arranged for an epicardial treatment of the LAA.

Once device 10 has been introduced into the patient, advancement and positioning may be performed through conventional imaging techniques, such as thoracoscopic or fluoroscopic imaging. In some embodiments, delivery device 12 may be compatible with imaging scopes which may be introduced through a selected lumen 14, 16 thereof.

As described above, the device of the present invention is arranged to occlude, for example, LAA 20 by pinching, cinching, crimping, clamping, compressing, or otherwise closing base 26 of LAA 20. In one embodiment, closing or "occluding" LAA 20 at base 26 is accomplished by securing an inner surface 28 of LAA 20 to itself substantially at base 26. Such securement effectively fluidly seals off an interior of LAA 20 from left atrium 22, and prevents blood clots from embolizing from within LAA 20 to left atrium 22. In some embodiments, the occlusion is of a character to cut off nutrient-providing blood supply to the tissue of LAA 20, thereby eventually resulting in necrosis and/or obliteration of LAA 20. In the illustrated embodiment, a means for effectuating occlusion of LAA 20 is implant 24, which may be detachably secured to delivery device 12 to remain indefinitely after delivery device 12 is removed from the patient.

In the embodiment illustrated in FIG. 1, a grasping device 18 may be employed to grasp and releasably hold LAA 20 to facilitate positioning and engagement of implant 24 at LAA 20. Grasping device 18 may typically comprise a conventional grasping tool, such as a suction tube which establishes negative pressure at a distal end 19 thereof, the negative pressure being suitable to releasably retain tissue, such as LAA 20 at distal end 19. Alternative grasping tools include thoracoscopic forceps and the like.

Figure 2:
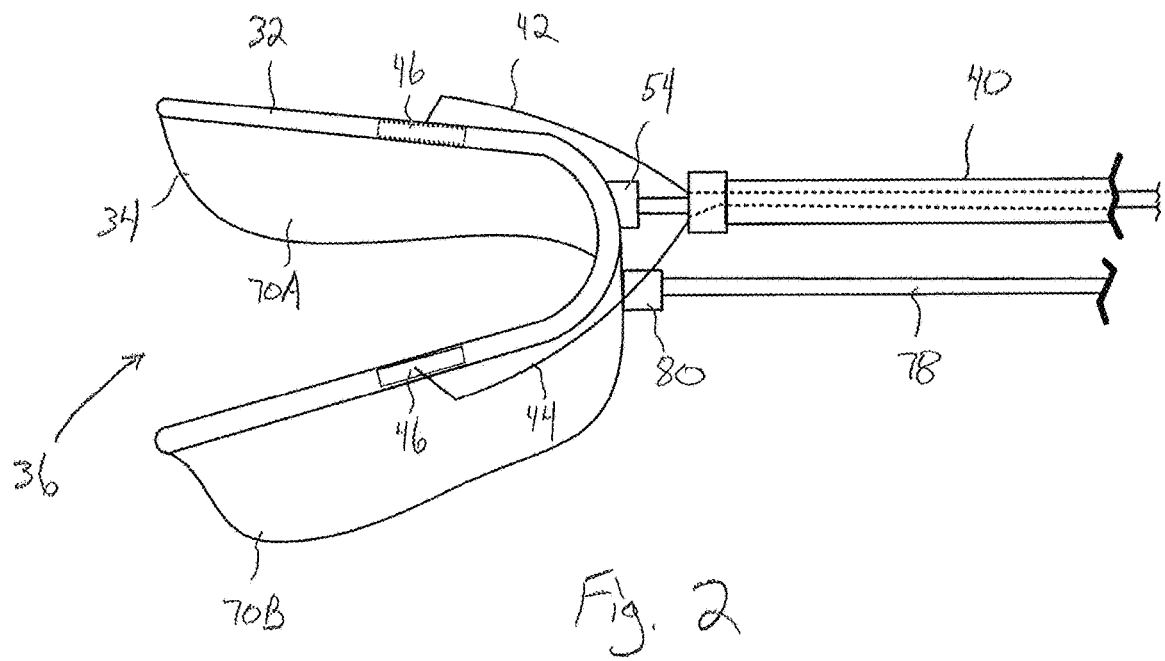
FIG. 2 is an isolation view of a portion of the atrial appendage occlusion device illustrated in FIG. 1.

An enlarged view of implant 24 is illustrated in FIG. 2, wherein implant 24 includes a clamp 32 and an inflatable cuff 34 attached to clamp 32. In some embodiments, clamp 32 is selectively adjustable between an open, undamped condition 36 (as illustrated in FIG. 2), and a closed, clamped position 38. Applicant contemplates a variety of mechanisms for selectively adjusting clamp 22 between the open and closed conditions 36, 38. For example, implant 24 may utilize a control arm 40, which incorporates the dual purpose of physically manipulating the spatial position of clamp 32, as well as selectively adjusting clamp 32 between open and closed conditions 36, 38. An example mechanism for effectuating such selective adjustment is illustrated in FIGS. 2A and 2B. In the illustrated embodiment, control arm 40 includes actuators 42, 44, which are detachably secured to clamp 32 at securement points 46. First and second actuators 42, 44 may be proximally controlled to move relative to one another generally along directions 48, 50 so as to adjust clamp 32 between open and closed conditions 36, 38. First and second actuators 42, 44 are also capable of rotating clamp 32 about an axis 52, and for turning clamp 32 into alignment with LAA 20. Such alignment enables first and second prongs 60, 62 to be placed at least partially about LAA 20.

In addition to, or in place of, the detachable securement of first and second actuators 42, 44 at securement points 46, control arm 40 may include a detachable link 54 which may be severed, opened, or otherwise released so as to disengage clamp 32 from control arm 40. Applicant contemplates a variety of mechanisms for detachably securing clamp 32 to control arm 40, with some of such mechanisms being conventionally understood by those of ordinary skill in the art.

Figure 3:
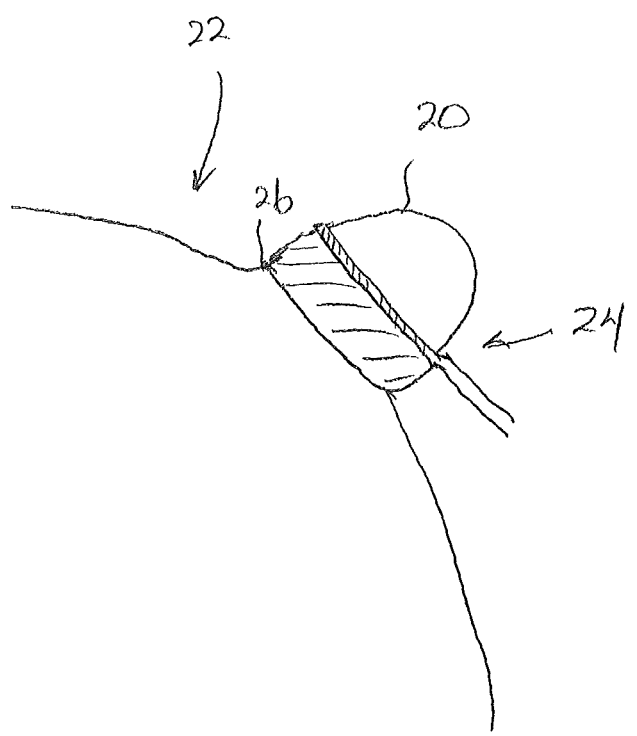
FIG. 3 is a schematic diagram of an atrial appendage occlusion device of the present invention engaged with a left atrial appendage.

As indicated above, implant 24 may be positioned at LAA 20 through thoracoscopic or fluoroscopic guidance. FIG. 3 illustrates an engagement of implant 24 with LAA 20. Implant 24 may be manipulated by, for example, first and second actuators 42, 44, so that first and second prongs 60, 62 of clamp 32 are positioned at substantially opposed sides 68, 70 of LAA 20, and about at least a portion of LAA 20.

Figure 3A:
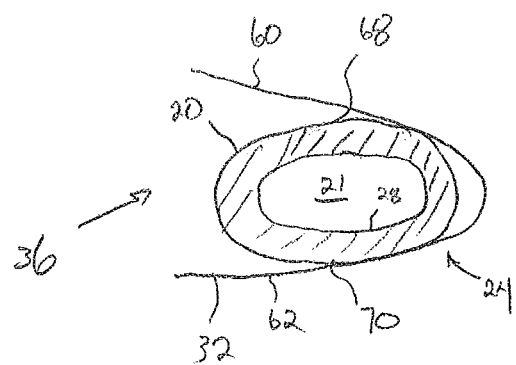
FIG. 3A is a schematic view of an atrial appendage occlusion device engaged with a left atrial appendage in an open condition.
Figure 3B:
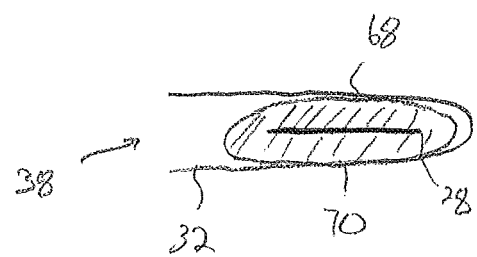
FIG. 3B is a schematic view of an atrial appendage occlusion device engaged with a left atrial appendage in a closed condition.

As illustrated in the schematic views of FIGS. 3A and 3B, LAA 20 includes a lumen 21 defined by inner surface 28. Implant 24 is engaged with LAA 20 initially while in an open condition 36, with first and second prongs 60, 62 of clamp 32 being positioned at substantially opposed sides 68, 70 of LAA 20. When clamp 32 is manipulated as described above from open condition 36 to closed condition 38, as illustrated in FIG. 3B, lumen 21 of LAA 20 may be substantially closed through the pressing together of opposed sides 68, 70 of LAA 20 to an extent that inner surface 28 is in contact with itself. The placement of clamp 32 in closed condition 38 may occlude LAA 20 by completely closing lumen 21. However, as described in greater detail hereinbelow, clamp 32 primarily serves as an anchoring element for inflatable cuff 34, such that inflatable cuff 34 is positioned and oriented to physiologically occlude LAA 20 at base 26.

In one aspect of the present invention, clamp 32 may be selectively adjusted between open and closed positions 36, 38 to not only anchor implant 24 at LAA 20, but to also facilitate the repositioning of implant 24 at LAA 20. For example, imaging techniques such as fluoroscopy and echocardiography may be utilized to assess whether inflatable cuff 34 is properly positioned to physiologically occlude LAA 20 at base 26. In the event that it is determined that the initial placement of implant 24 is incorrect for a preferred occlusion of LAA 20, an adjustment mechanism, such as first and second actuators 42, 44 of control arm 40 may reopen clamp 32 from closed condition 38 to open condition 36, and thereafter reposition clamp 32 at LAA 20. Once the position of clamp 32 (and implant 24) has been adjusted, clamp 32 may again be modified from open condition 36 to closed condition 38 to securely anchor implant 24 at LAA 20. Such adjustability of clamp 32, and correspondingly implant 24, is facilitated through the detachable connection of control arm 40 to clamp 32. The detachable connection, as described above, enables proximal control to repeatedly adjust clamp 32 between open and closed conditions 36, 38, including from open condition 36 to closed condition 38, and from closed condition 38 to open condition 36. Such adjustment of clamp 32 may be repeated several times if necessary to appropriately position and orient implant 24 at LAA 20.

Clamp 32 may be fabricated from a variety of biocompatible materials, such as stainless steel, titanium, and other metallic, alloy, and non-metallic materials. In some embodiments, clamp 32 may be formed of a resilient material, thereby continuing to apply direct pressure to LAA 20 enclosed within clamp 32 in closed condition 28. Because clamp 32 primarily serves as an anchoring device, clamp 32 need not be of specific structural capacity, and may therefore exhibit a relatively low profile for ease of delivery and placement at LAA 20.

Figures 4A, 4B:
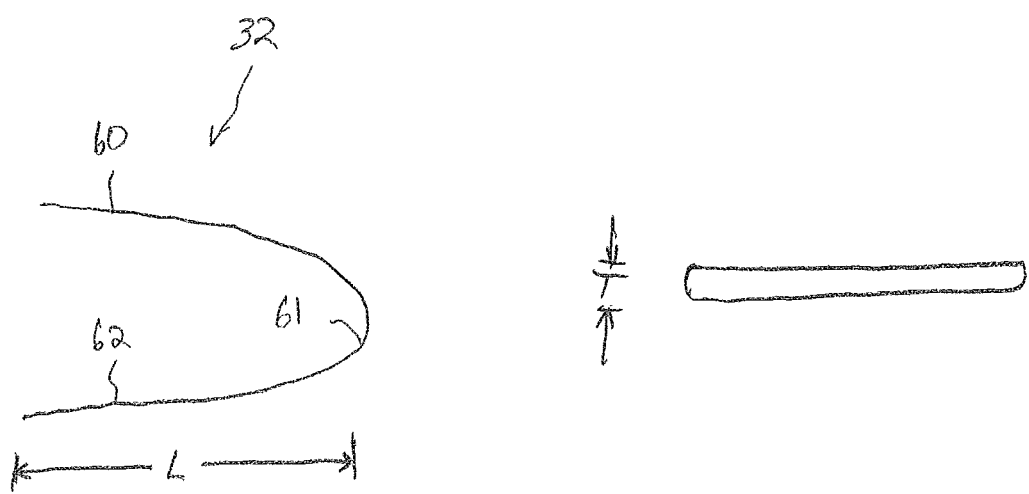
FIG. 4A is an isolation view of a portion of the atrial appendage occlusion device illustrated in FIGS. 1 and 2 in an open condition.
FIG. 4B is an isolation view of a portion of the atrial appendage occlusion device illustrated in FIGS. 1 and 2 in a closed condition.

As illustrated in FIGS. 4A and 4B, clamp 32 includes first and second prongs 60, 62 emanating from central portion 61. First and second prongs 60, 62 may be the same or different curvatures forming various shapes, including an opening with tapered ends, oval, ovoid, crescent, etc. Prong length "L" may be equal or different as between first and second prongs 60, 62, and may be provided in various sizes as physiologically appropriate. For example, prong length "L" may be between about 1-5 cm, though other sizes are contemplated as being useful in the present invention. Moreover, prong thickness "T" may be even or uneven along first and second prongs 60, 62, and may be between, for example, about 0.1-5 mm.

Clamp 32 may also include tissue engaging projections and fasteners, such as spikes, staples, rivets, sutures, and clips extending from one or both of first and second prongs 60, 62. The tissue fasteners may be formed of a resilient, elastic, superelastic, metallic, alloy, or non-metallic material. The tissue fasteners may be integrally formed with clamp 32, mounted within clamp 32, or mounted within a device that may be attached to clamp 32.

The repositionability of clamp 32 is advantageous for precisely positioning inflatable cuff 34 at LAA 20, such that inflation of cuff 34 physiologically occludes LAA 20 at base 26. For the purposes hereof, the term "physiologically occludes" is intended to mean the substantially complete closure or occlusion of lumen 21 of LAA 20 to an extent appropriate to prevent the formation of clot and the release of emboli from the appendage. Therefore, "physiological occlusion" may include any closure of LAA 20 which is effective in the prevention of clot formation and the release of emboli therefrom, and need not comprise the closure of the entirety of lumen 21 of LAA 20. In some embodiments, "physiologically occludes" may refer to a closure of lumen 21 at or near base 26 with such closure constituting intimate contact of inner surface 28 at or near base 26 to an extent appropriate to prevent blood flow into and out from LAA 20.

Inflatable cuff 34 includes one or more portions 70A, 70B that may be selectively inflated with a fluid, such as saline, to inwardly press upon LAA 20 to an extent appropriate to physiologically occlude LAA 20. To selectively inflate inflatable cuff 34, implant 24 includes a fluid supply tube 78 that is detachably secured to inflatable cuff 34. Fluid supply tube 78 may be configured for selectively conveying pressurized fluid such as saline to inflatable cuff 34 through a one way valve 80 which permits fluid flow into, but not out from, inflatable cuff 34. Fluid supply tube 78 is preferably deliverable along with implant 24 through a lumen 16 of delivery device 12.

Figure 5A:
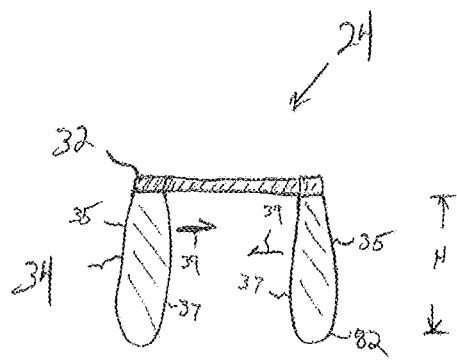
FIG. 5A is an isolation elevational view of a portion of the atrial appendage occlusion device illustrated in FIGS. 1 and 2.

In some embodiments, inflatable cuff 34 defines one or more balloon structures defining respective portions 70A, 70B, with the balloon structures employing a resiliently elastic skin which may be resiliently expanded upon inflating fluid flow from fluid supply tube 78 into respective chambers thereof. As illustrated in FIG. 5A, inflatable cuff 34 may include relatively rigid outer walls 35 with relatively elastic and non-rigid inner walls 37. In such a manner, inflation of inflatable cuff 34 causes expansion of inflatable cuff 34 inwardly along direction arrows 39. Such inward expansion of inflatable cuff 34 effectuates the occlusion of LAA 20.

Inflatable cuff 34 may be fabricated from a variety of materials to provide the functionality described above. In particular, inflatable cuff 34 may include a skin layer 82 which is manufactured from one or more materials to provide zoned characteristics. As described above, a first material for skin layer 82 may be substantially rigid at outer surface 35, while a different material may be provided at an inner surface 37. In other embodiments, reinforcement materials or devices may be employed to promote inward expansion of cuff 34 upon inflation thereof. Such reinforcement materials or devices may be disposed at or adjacent to outer surface 35 of inflatable cuff 34 to limit outwardly-directed expansion.

Inflatable cuff 34 may be secured to clamp 32 at one or more points along clamp 32. In some embodiments, inflatable cuff 34 is secured to the entire length of clamp 32. In other embodiments, however, inflatable cuff 34 may extend only partially along clamp 32, and may include discontinuous portions along clamp 32. A variety of securement mechanisms are contemplated by the present invention to secure inflatable cuff 34 to clamp 32. Example mechanisms include adhesives, fasteners, and other mechanisms, including conventional mechanisms for securing inflatable cuff 34 to clamp 32.

Inflatable cuff 34 may include one or more distinct chambers that are sequentially or simultaneously filled with inflation fluid supplied through fluid supply tube 78. In one embodiment, for example, inflatable cuff 34 may include a plurality of chambers which are filled through an "overflow" concept in which a secondary chamber is filled only after a primary chamber is completely filled with fluid. In some embodiments, each portion 70A, 70B of inflatable cuff 34 may be filled with between about 1-10 cc of fluid.

Figure 5B:
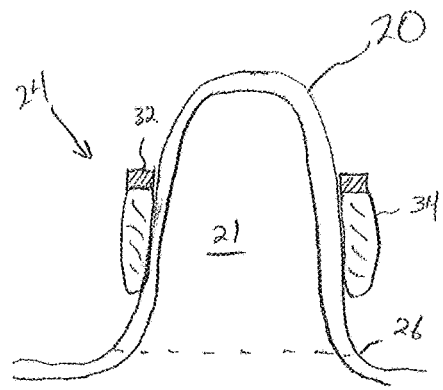
FIG. 5B is a schematic view of an atrial appendage occlusion device in engagement with a left atrial appendage.

An occlusion sequence utilizing implant 24 is illustrated in FIGS. 5B-5E, in which implant 24 is placed about LAA 20 in an open condition 36. Positioning of implant 24 at LAA 20 may be verified through echocardiography and fluoroscopy. FIG. 5B illustrates an improper positioning of implant 24, in that inflatable cuff 34 does not extend to base 26 of LAA 20, where occlusion is desired. In one embodiment, clamp 32 may be adjusted to a closed condition 38 at the position illustrated in FIG. 5B, followed by position verification through echocardiography and/or fluoroscopy. When it is determined that the position and/or orientation of implant 24 is incorrect, clamp 32 may be re-adjusted to an open condition 36 for re-positioning of implant 24. as described above.

Figure 5C:
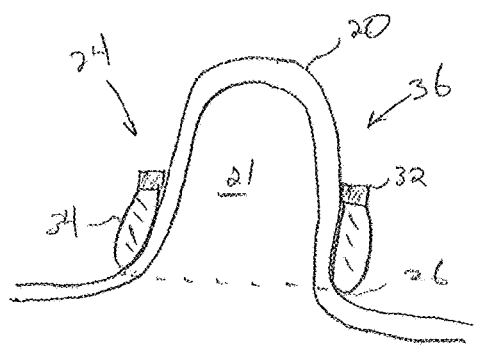
FIG. 5C is a schematic view of an atrial appendage occlusion device in engagement with a left atrial appendage.
Figure 5D:
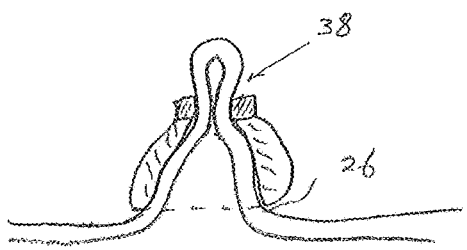
FIG. 5D is a schematic view of an atrial appendage occlusion device m engagement with a left atrial appendage in a closed condition.

Implant 24 may be re-positioned, as illustrated in FIG. 5C. Here, inflatable cuff 34 extends substantially to base 26 of LAA 20. Confirmation of such appropriate position and orientation may be performed, for example, subsequent to adjustment of clamp 32 to a closed condition 38, such as is illustrated in FIG. 5O.

Figure 5E:
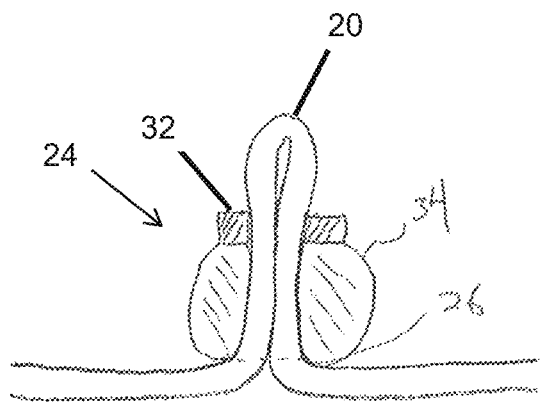
FIG. 5E is a schematic view of an atrial appendage occlusion device in occlusive engagement with a left atrial appendage.

Once the appropriate position of implant 24 has been confirmed, fluid is directed through fluid supply tube 78, and through one-way valve 80 into inflatable cuff 34 to thereby expand inflatable cuff 34 to an extent appropriate to physiologically occlude LAA 20 at base 26. FIG. 5E illustrates such occlusion subsequent to inflation of inflatable cuff 34. Sufficient occlusion of LAA 20 may be confirmed through echocardiography and/or fluoroscopy. If, for example, further closure of LAA 20 is required to accomplish physiological occlusion, additional fluid may be added to inflatable cuff 34 through fluid supply tube 78.

Figure 5F:
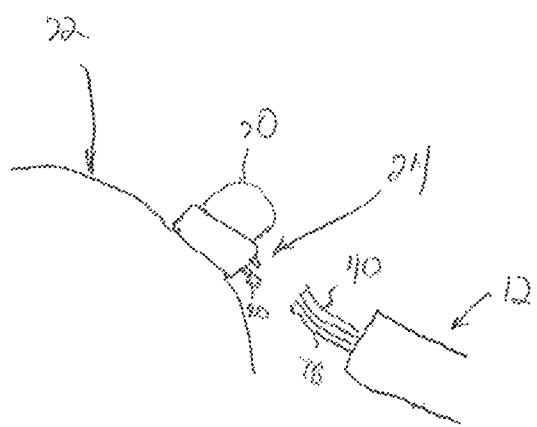
FIG. 5F is a schematic view of an atrial appendage occlusion device with an implant portion separated from a delivery device.

Once appropriate occlusion has been confirmed, control arm 40 may be detached from clamp 32 as described above. Moreover, fluid supply tube 78 may be separated from inflatable cuff 34, preferably upstream from one-way valve 80 so as to maintain fluid pressure within inflatable cuff 34. An illustration of implant 24 at LAA 20 subsequent to separation from control arm 40 and fluid supply tube 78 is shown in FIG. 5F. A variety of mechanisms are contemplated for separating fluid supply tube 78 from inflatable cuff. In one embodiment, a thoracoscopic scissor maybe guided through delivery device 12 to cut fluid supply tube 78 at a location proximal to one-way valve 80. Subsequent to the separation, the thoracoscopic scissor, fluid supply tube 78, and control arm 40 may be withdrawn through respective lumens 14, 16 of delivery device 12, and the delivery device 12 may thereafter be withdrawn from the patient. Consequently, implant 24 may be left at LAA 20 indefinitely to ensure physiological occlusion thereof.

In one embodiment, inflatable cuff 34 is detachably secured to clamp 32, such that subsequent to confirmation of physiological occlusion of LAA 20 by inflatable cuff 34, clamp 32 may be detached from inflatable cuff 34, and withdrawn from the procedure site through delivery device 12. In such an embodiment, only inflatable cuff 34 is left at LAA 20 following the occlusion procedure. Therefore, it is to be understood that clamp 32 primarily acts as an anchoring mechanism, while inflatable cuff 34 performs the occlusion of LAA 20. Inflatable cuff 34 may assume a variety of configurations, and in one embodiment may have a height "H" of about 0.22 cm. Other sizes, however, of inflatable cuff 34 may be employed in implant 24 of the present invention.

For the purposes hereof, the term "cuff" is not intended to be exclusive of the various inflatable or otherwise expandable bodies useful in the present application. To that end, other terms may be interchangeably utilized to describe inflatable cuff 34. Example alternative terms include bladder, balloon, diaphragm, vessel, skirt, tube, and the like. Moreover, inflatable cuff 34 may be selectively and adjustably expandable through means other than inflation, including various mechanical expansion means to constrict the LAA 20 to an occlusive extent.

Figure 6A:
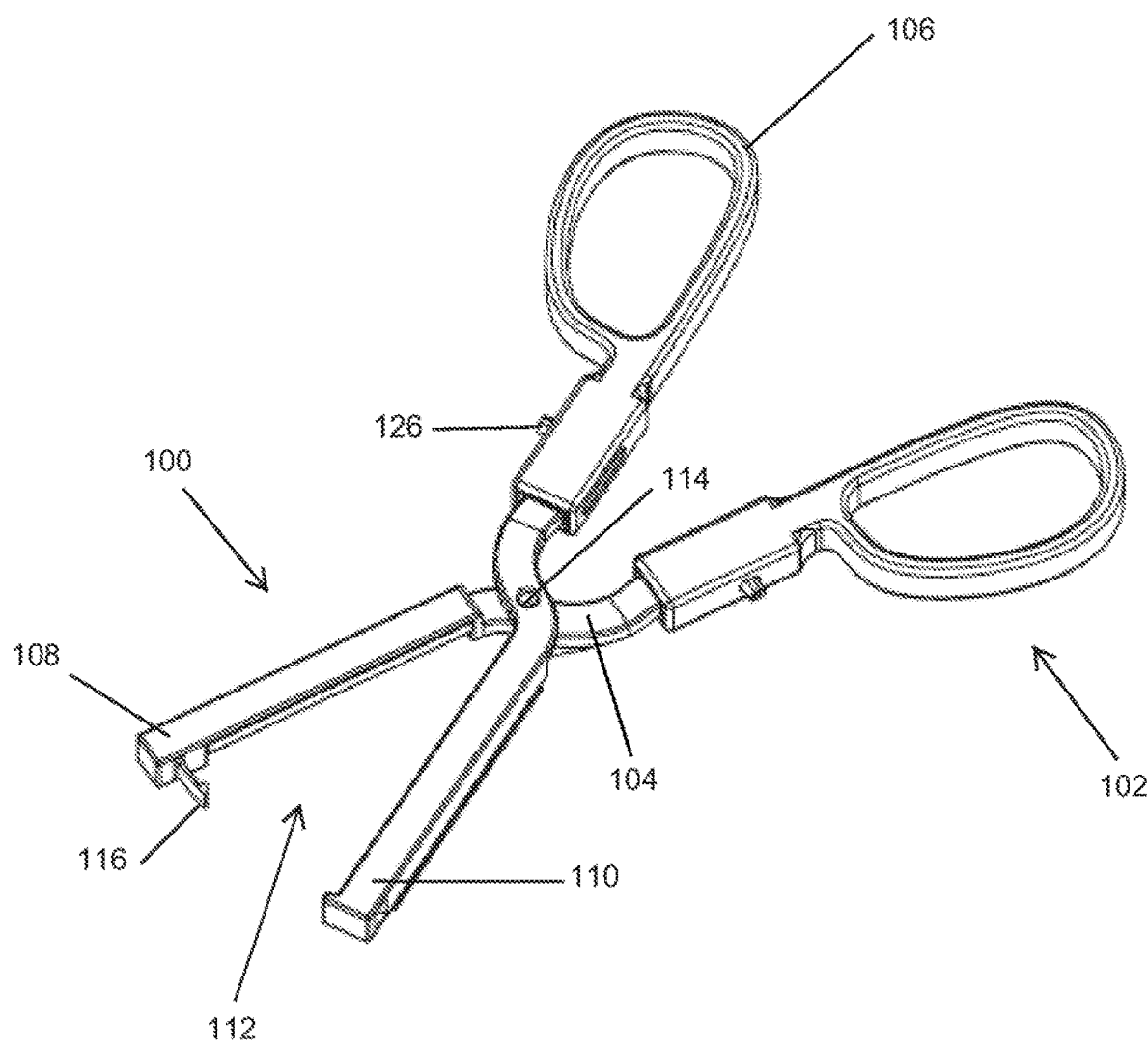
FIG. 6A depicts an isometric view of an epicardial implant system according to embodiments.
Figure 6B:
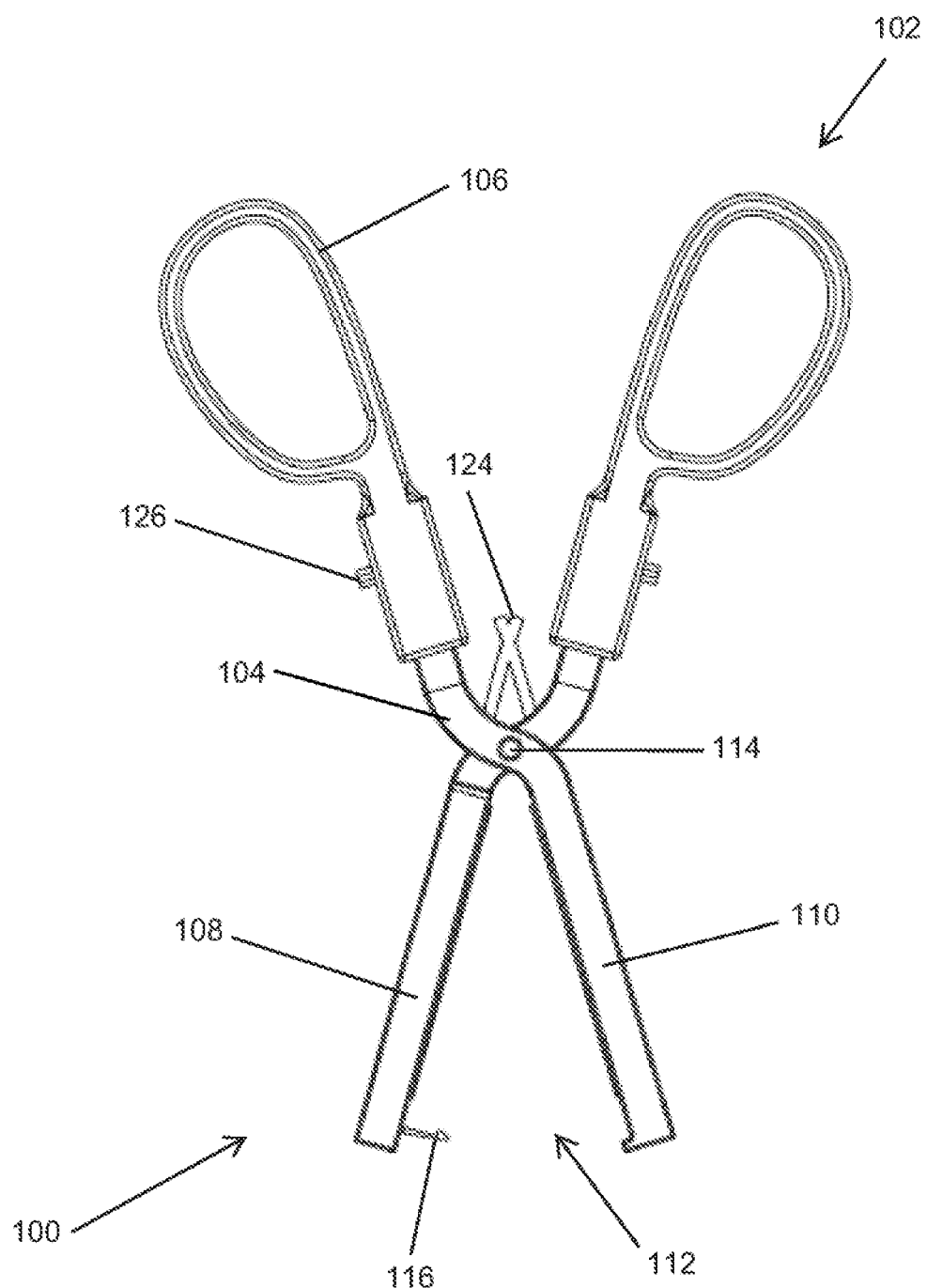
FIG. 6B depicts a top view of the epicardial implant system of FIG. 6A in an open state according to embodiments.

FIGS. 6A-6L depict another embodiment of an epicardial implant 100 and delivery device 102. As seen in FIG. 6A, delivery device 102 enables a user to manipulate a positioning device 104 of the implant 100 about the atrial appendage. For example, delivery device 102 includes a handle 106 that is configured to pivot a first prong 108 and a second prong 110 of the positioning device 104 toward and away from one another. For example, handle 106 may be scissor-like and include two members that are coupled with a hinge or pivot point 114 that allows a user to open and close the prongs 108 and 110. A user, such as a surgeon or other medical personnel, may use the handle 106 to position the first prong 108 and the second prong 110 around a base of an atrial appendage such that the atrial appendage is disposed within an open interior 112 of the positioning device 104. Open interior 112 is formed between the first prong 108 and the second prong 110 as shown in FIG. 6B. While shown with pivot point 114 being a part of positioning device 104, it will be appreciated that in some embodiments, the pivot point 114 may be disposed on the handle 106.

Figure 6C:
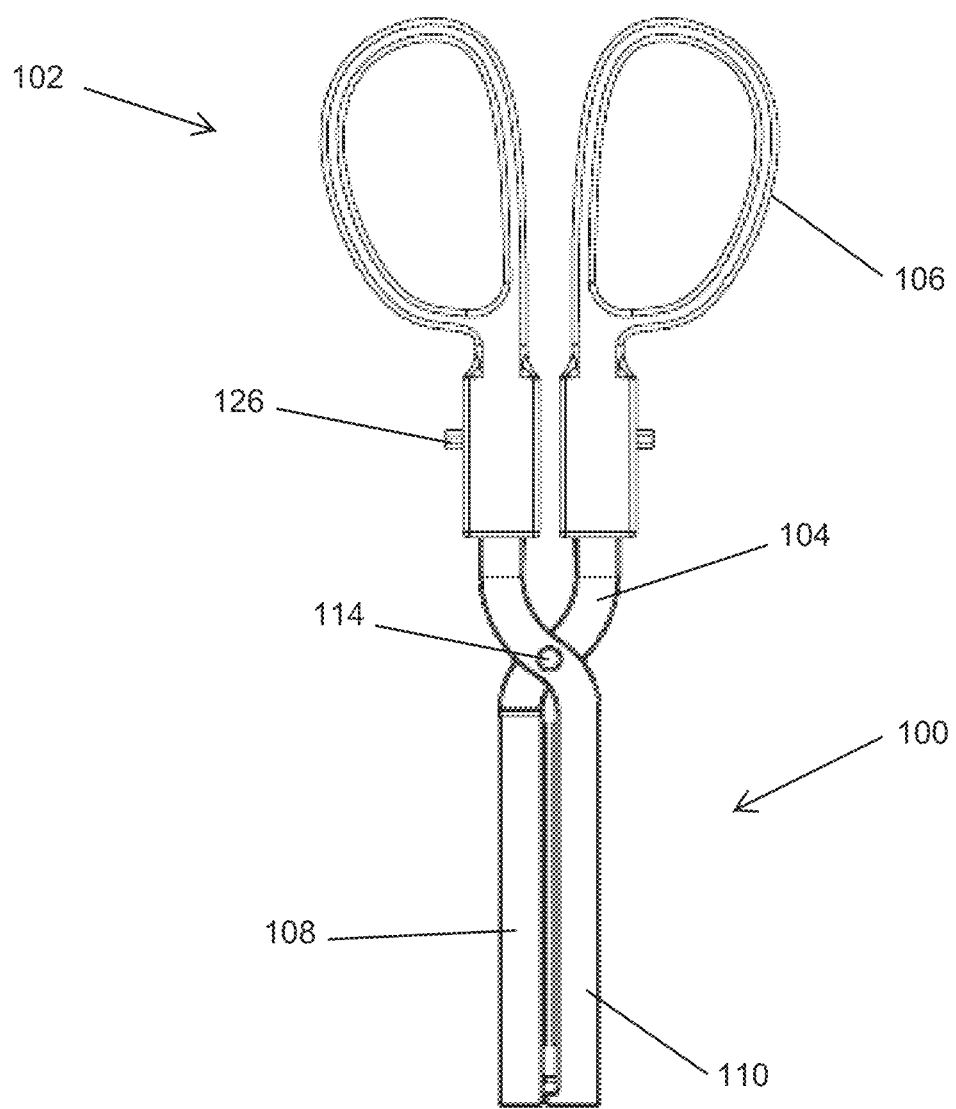
FIG. 6C depicts a top view of the epicardial implant system of FIG. 6A in a closed state according to embodiments.
Figure 6D:
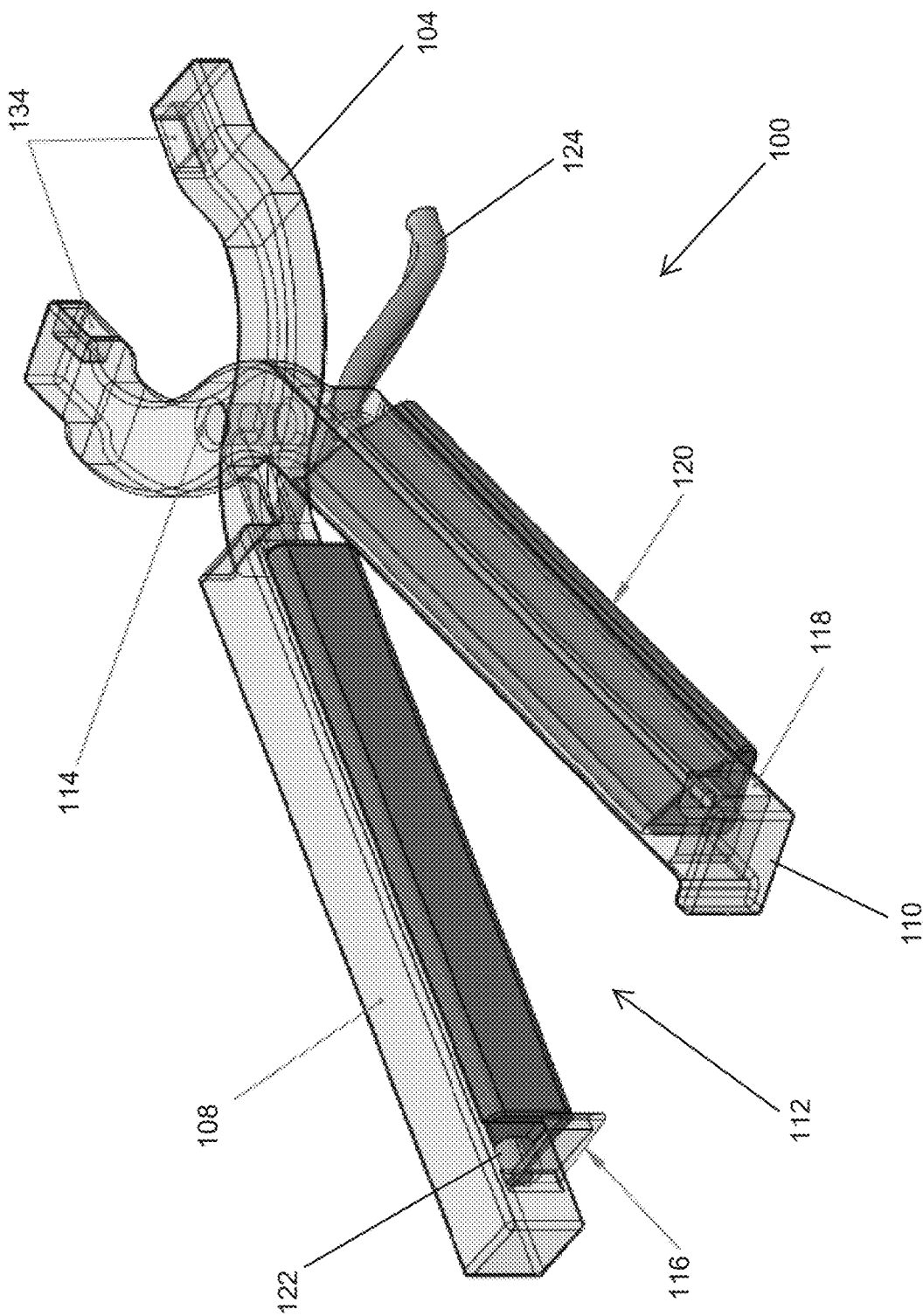
FIG. 6D depicts an isometric view of a positioning device of the epicardial implant system of FIG. 6A according to embodiments.

Once the positioning device 104 is in the proper location, the handle 106 may be used to close the positioning device 104 around the atrial appendage. For example, a user may pivot the two handle members toward one another about pivot point 114 to bring the first prong 108 and the second prong 110 into close proximity, oftentimes in a parallel or near parallel (within about 5° of parallel) state as shown in FIG. 6C. In some embodiments, an inner surface of the positioning device 104 may be configured to only lightly contact the surface of the atrial appendage when closed to maintain a general position of the positioning device 104. In other embodiments, when closed the positioning device 104 is secured with greater pressure against the atrial appendage such that the atrial appendage is pinched between the first prong 108 and the second prong 110. When closed, a distal end of the positioning device 104 may clasp or latch to maintain the prongs 108 and 110 in a desired position. For example, a distal end of one or both of the prongs 108 and 110 may form a clasp or latch. In one particular embodiment, the first prong 108 may include a latch extension 116 that is configured to engage with a corresponding receptacle 118 of the second prong 110. Receptacle 118 is shown in FIG. 6D and may include a recess that receives a protrusion of the latch extension 116 to lock the latch extension 116 in place. It will be appreciated, however, that other securement mechanisms may be used, and in some embodiments, the location of the latch and the receptacle may be reversed.

In practice, a user may not get the placement of the positioning device 104 correct on the first attempt. The positioning device 104, including the latch extension 116, may be configured to be re-opened such that the positioning device 104 can be repositioned. For example, the latch extension 116 and receptacle 118 may be configured to disengage upon application of a predetermined amount of force applied via the handle 106. In other embodiments, the latch mechanism may include a disengagement actuator that releases the latch extension 116 from the recess 118. The positioning device 104 may be opened and closed any number of times to ensure that a proper placement of the positioning device 104 is achieved. Once closed, the positioning device 104 may form a closed circuit surrounding the open interior 112, with the first prong 108 and second prong 110 serving as elongated side members and the distal end and hinge or other pivot point 114 forming end members. In some embodiments where the pivot point 114 is part of the handle 106 rather than the positioning device 104, the positioning device 104 may close only three sides of the open interior, with an end opposite the distal end remaining open.

The positioning device 104 may house one or more expandable cuffs 120. For example, the first prong 108 and the second prong 110 may each define a cuff housing 122. The cuff housing 122 may be a recess formed within an interior surface of each prong 108 and 110 that is sized and shaped to receive an uninflated cuff 120. Cuffs 120 be formed from similar materials and may have similar features as cuffs 34 described in relations to FIGS. 1-5 above. As just a one example, cuff 120 may define one or more balloon structures, with the balloon structures employing a resiliently elastic skin which may be resiliently expanded upon the filling of an internal reservoir. Cuff 120 may include relatively rigid outer walls with relatively elastic and non-rigid inner walls. Cuff 120 may be secured to the positioning device 104 at one or more points along a length of the positioning device 104. Each cuff 120 may include one or more distinct chambers that are sequentially or simultaneously filled with inflation fluid supplied through fluid supply tube.

When expanded, the cuffs 120 may be any shape or size to press and/or squeeze against the atrial appendage to physically occlude the appendage. For example, in some embodiments, the cuffs 120 may have a triangular cross-sectional shape, with at least one separate cuff 120 being disposed in each of the prongs 108 and 110. In some embodiments, the cuffs 120 will be oriented such that parallel surfaces of the triangular cuff(s) in the first prong 108 and the triangular cuff(s) in the second prong 110 face one another, although other orientations may be possible. It will be appreciated that other shapes of cuffs 120 may be used. For example, cuffs 120 may have rectangular, square, circular, and/or other cross-sectional shapes that constrict and occlude the atrial appendage. Additionally, in some embodiments the cuffs 120 within the first prong 108 and the second prong 110 may have different shapes.

Each cuff 120 may be expanded by filling an internal reservoir of the cuff 120 with a fluid. For example, saline and/or another fluid may be introduced into the reservoir via one or more fluid supply tubes 124. In some embodiments, the fluid may be introduced gradually, which allows the implant 100 to be repositioned if necessary, without damaging the contacting heart tissue. To ensure that the fluid does not leak out of the cuff 120, the fluid supply tubes 124 may each include a one-way valve (not shown) that permits the fluid to be introduced into the reservoir, but prevents the fluid from escaping the reservoir. In other embodiments, a clip or other clamping device may be secured around a portion of the fluid supply tube to cinch or squeeze the outer walls of the tube together, thereby sealing the interior of the tube. This allows the cuff 120 to be deflated again by removing the clip and allowing the fluid to escape the cuff 120. Deflation of the cuff 120 may be necessary if the positioning device 104 moves out of a proper position. In some embodiments, a portion of the fluid supply tube may be burned off after the cuffs 120 have been inflated. This may serve to remove any excess tubing, as well as to melt the remaining tube shut to seal the cuffs 120.

Figure 6E:
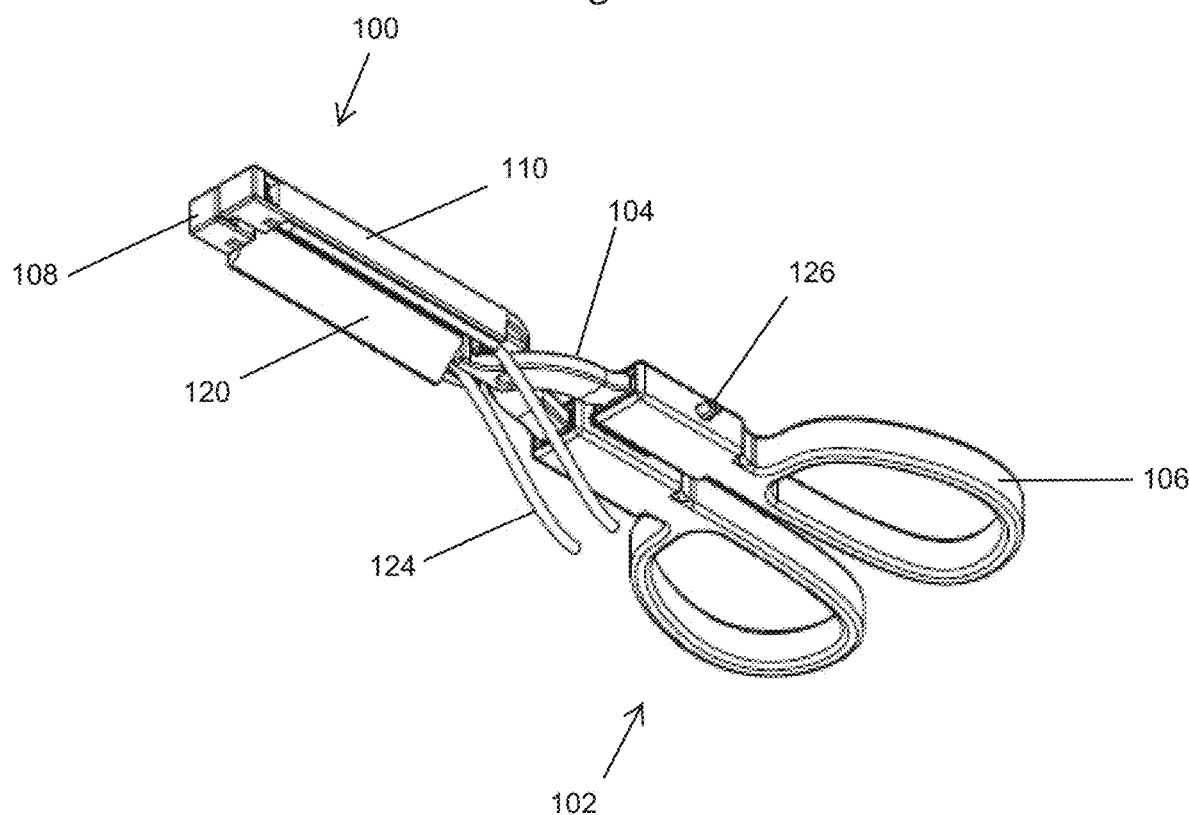
FIG. 6E depicts a bottom isometric view of the epicardial implant system of FIG. 6A in an unexpanded state according to embodiments.
Figure 6F:
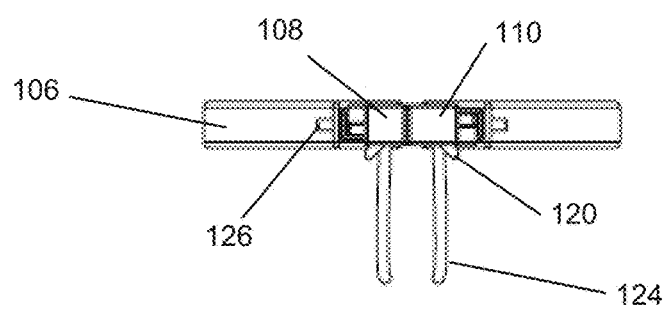
FIG. 6F depicts a front view of the epicardial implant system of FIG. 6A in an unexpanded state according to embodiments.
Figure 6G:
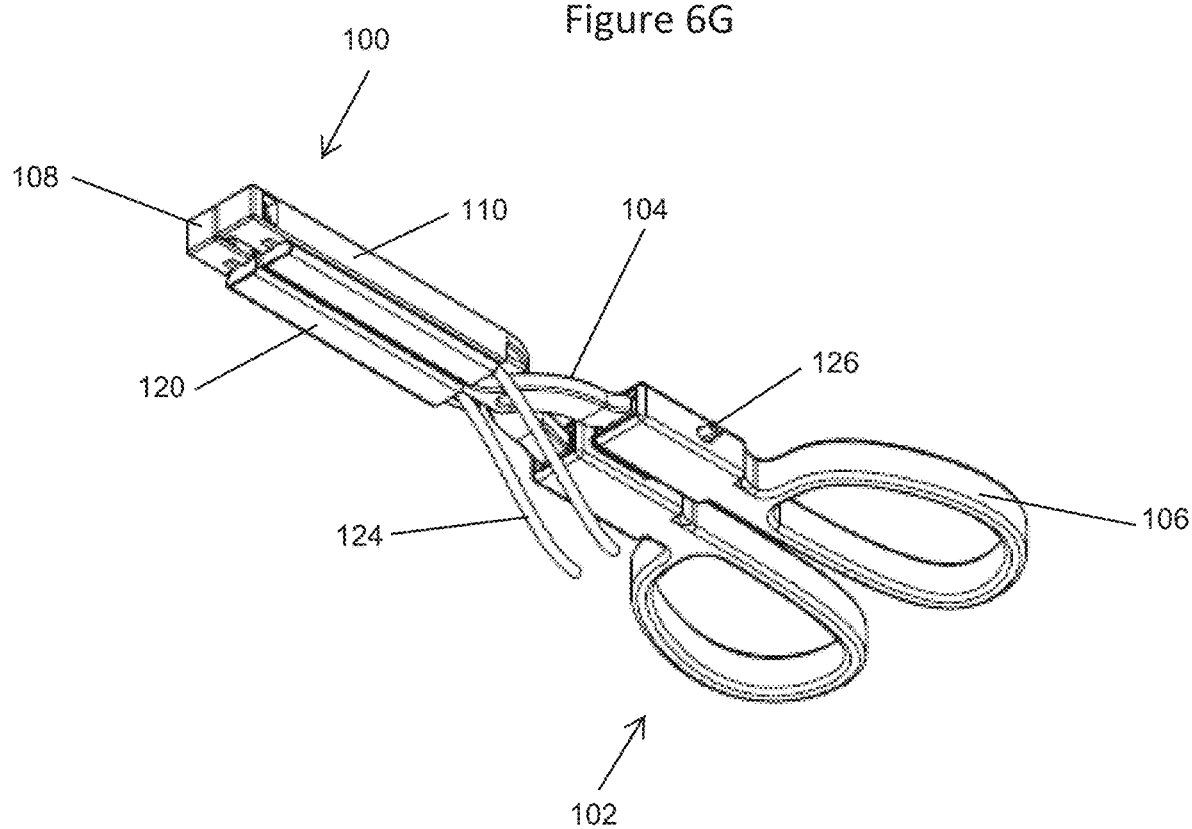
FIG. 6G depicts a bottom isometric view of the epicardial implant system of FIG. 6A in an expanded state according to embodiments.
Figure 6H:
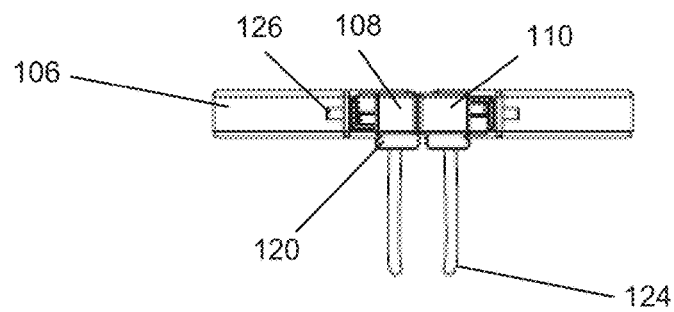
FIG. 6H depicts a front view of the epicardial implant system of FIG. 6A in an expanded state according to embodiments.

During the placement of the positioning device 104, the cuffs 120 are maintained in an uninflated state as shown in FIGS. 6E and 6F. This allows the implant 100 to be repositioned until a proper placement relative to the atrial appendage is achieved. Here, triangular cuffs 120 are shown in an uninflated state where inner surfaces of the cuffs 120 are at an angle relative to one another and are not close enough to one another to occlude the atrial appendage. Once the user has determined that the positioning device 104 is properly placed, the cuffs 120 may be expanded by introducing fluid into the reservoir of each cuff 120. This inflates or otherwise expands the cuffs 120 into the open interior 112 of the positioning device 104 such that the atrial appendage is squeezed, cinched, and/or otherwise occluded by the cuffs 120. As shown in FIGS. 6G and 6H, the expanded triangular cuffs 120 are expanded such that the interior-facing surfaces of each cuff 120 are generally parallel to one another and are in close proximity to one another to occlude the atrial appendage, although other configurations are possible.

Figure 6I:
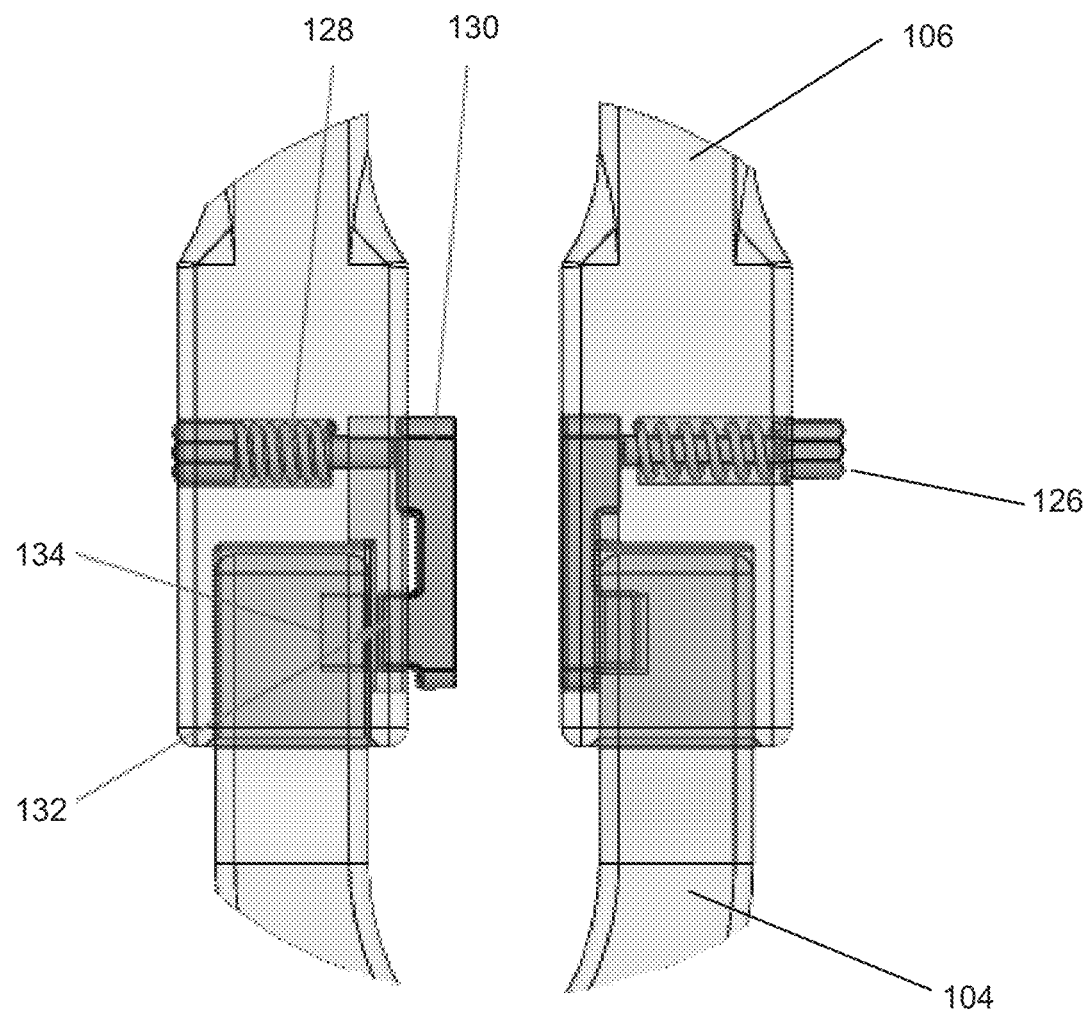
FIG. 6I depicts a top cross-sectional view of a quick release mechanism of the epicardial implant system of FIG. 6A according to embodiments.
Figure 6J:
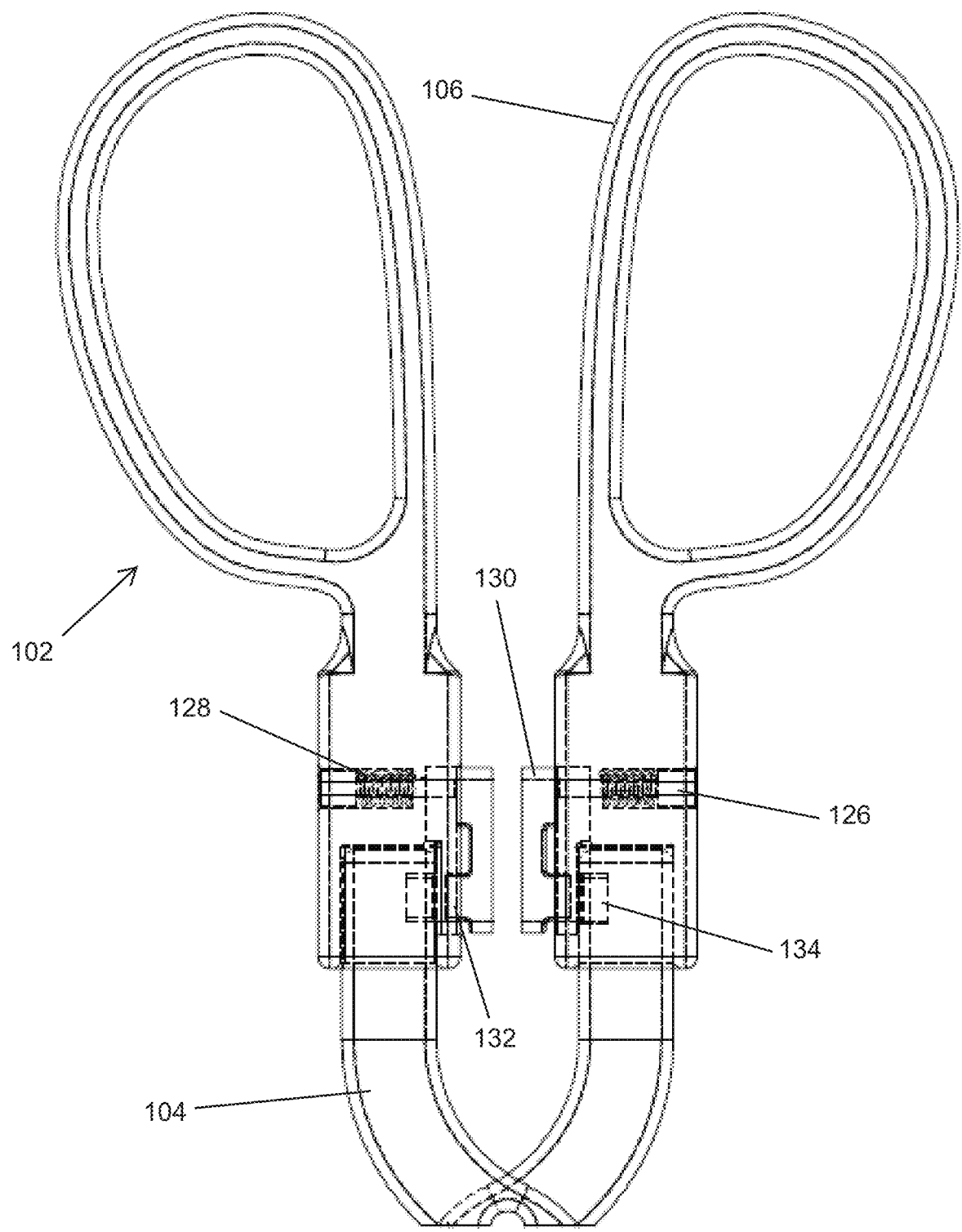
FIG. 6J depicts a top cross-sectional view of a quick release mechanism of the epicardial implant system of FIG. 6A according to embodiments.
Figure 6L:
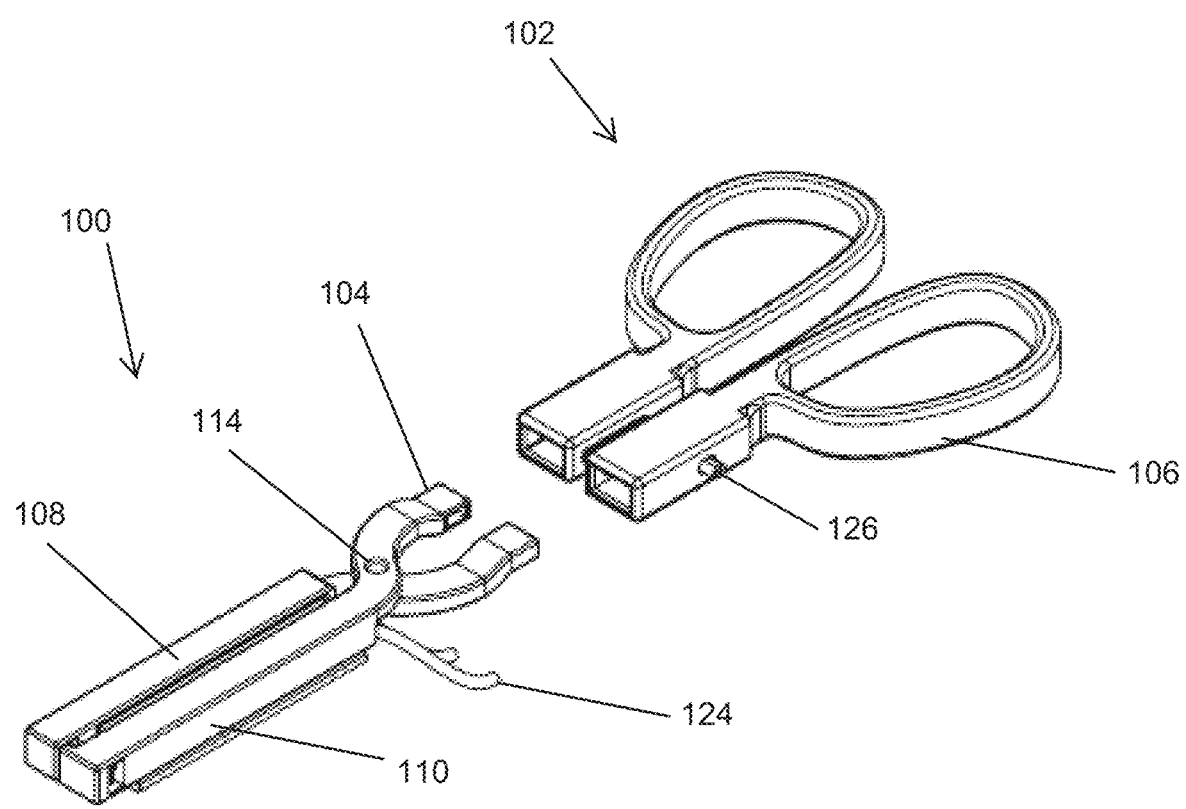
FIG. 6L depicts an isometric view of the epicardial implant system of FIG. 6A with a delivery device and a positioning device disengaged from one another according to embodiments.

Once the cuffs 120 have been expanded, the implant 100, including both the positioning device 104 and the cuffs 120, may be detached from the delivery device 102. For example, the handle 106 may include a quick release mechanism that allows the implant 100 to be quickly disengaged. In one embodiment, each member of handle 106 may include a depressible actuator, such as a button 126. In an engaged position, button 126 may extend outward through an opening in the handle 106. As shown in FIG. 6I the button 126 may be biased outward, such as using a spring 128 positioned within the handle 106. Button 126 may be coupled with and/or formed integral with a magazine catch 130. Magazine catch 130 is configured to be received within a recess formed within the handle 106 and may include a catch boss 132 that extends from a main body of the magazine catch 130. The catch boss 132 may engage within a catch recess 134 formed within the position device 104. When depressed, the button 126 forces the magazine catch 130 and catch boss 132 to move away from the catch recess 134, thereby releasing the handle 106 from the positioning device 104 as shown in FIGS. 6I and 6J. In some embodiments, a portion of the magazine catch 130 may extend through an opening formed in the handle 106 when the button 126 is depressed as shown in FIG. 6K. Once the quick release mechanism has been actuated, each of the members of handle 106 may be separated from the implant 100 as shown in FIG. 6L, allowing the implant 100 to remain attached to the atrial appendage. To detach the cuffs 120, it may be necessary to clip or otherwise cut the fluid supply tube. This may be done at a position upstream of the one-way valve and/or clip to ensure that the cuffs 120 remain inflated.

In some embodiments, both handle members may include the quick release mechanism. In such embodiments, the buttons 126 may be actuated simultaneously and/or individually. This allows the handle members to be detached from the implant 100 at the same time or one by one. It will be appreciated that other quick release mechanisms may be utilized to releasable couple the handle 106 and the implant 100. It will also be appreciated that the quick release mechanism may be reversed such that the actuator is on the implant 100 rather than the delivery device 102.

In some embodiments, the handle 106 may be adjustable and/or configured to be at an angle relative to the positioning device 104 such that the two components are not co-planar. For example, the handle 106 may be pivoted or otherwise attached to the positioning device 104 at an angle of between about 0° and 90°. Such orientations may allow the surgical team an easier angle to view and manipulate the positioning device 104.

Figure 7A:
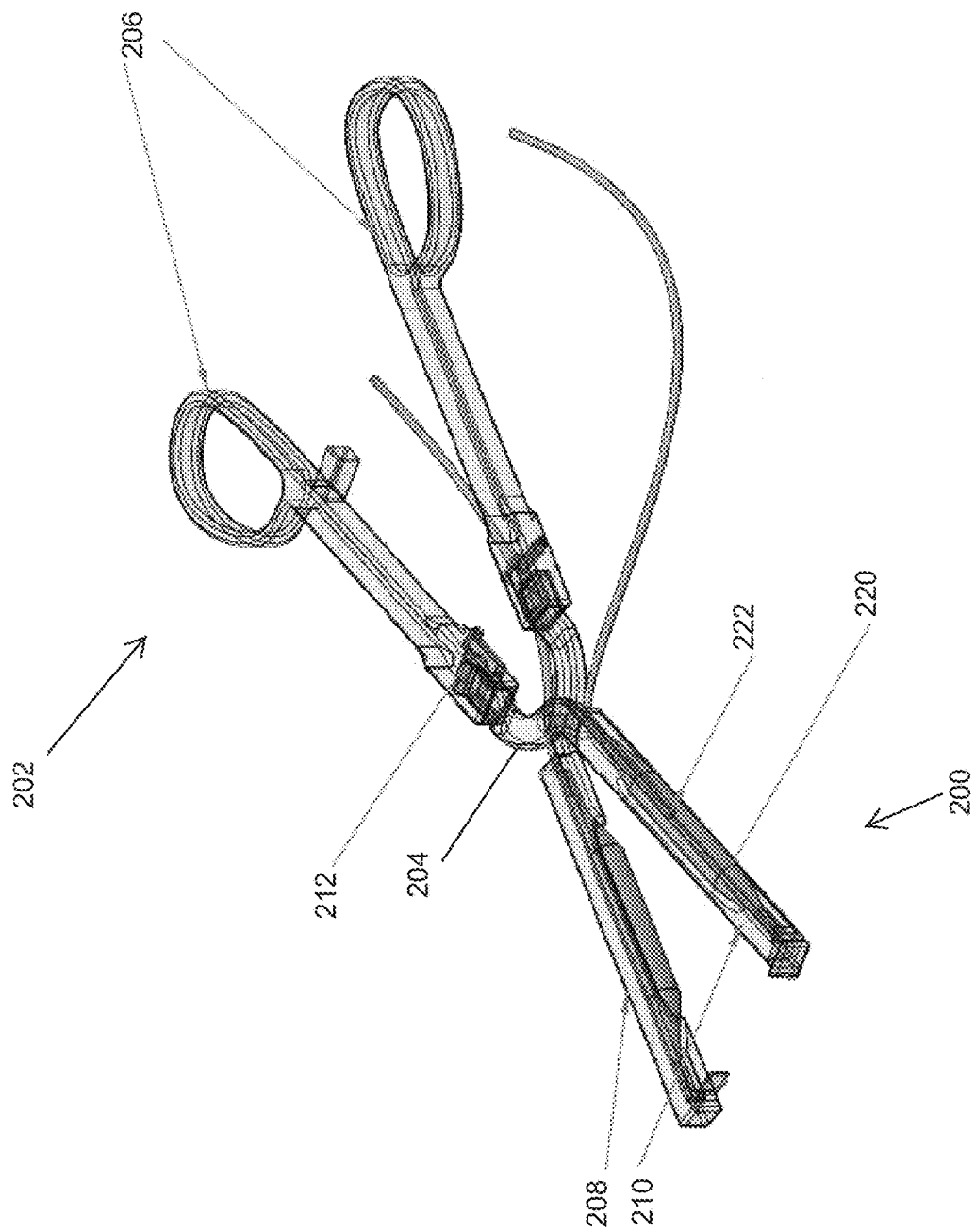
FIG. 7A depicts an isometric view of an epicardial implant system according to embodiments.

FIGS. 7A-7C depict another embodiment of an implant 200 and delivery device 202 that uses circular cuffs 220. Implant 200 and delivery device 202 may be constructed similarly to those described in relation to FIGS. 6A-6L. For example, as shown in FIG. 7A, delivery device 202 may include handle 206 and a quick release mechanism 212 similar to that of delivery device 102. Implant 200 includes a positioning device 204 having a first prong 208 and a second prong 210 that may be pivoted relative to each other between an open state and a closed state. Each prong 208 and 210 defines a cuff housing 222, such as a recess that is sized and shaped to receive the unexpanded cuff 220 as shown in FIG. 7B. Once the positioning device 204 has been placed about the base of the atrial appendage, the cuffs 220 may be expanded as shown in FIG. 7C. Here, circular cuffs 220 are expanded such that the inner-facing surfaces of each cuff 220 are positioned proximate to one another, allowing the cuffs 220 to pinch or otherwise occlude the atrial appendage.

Figure 8A:
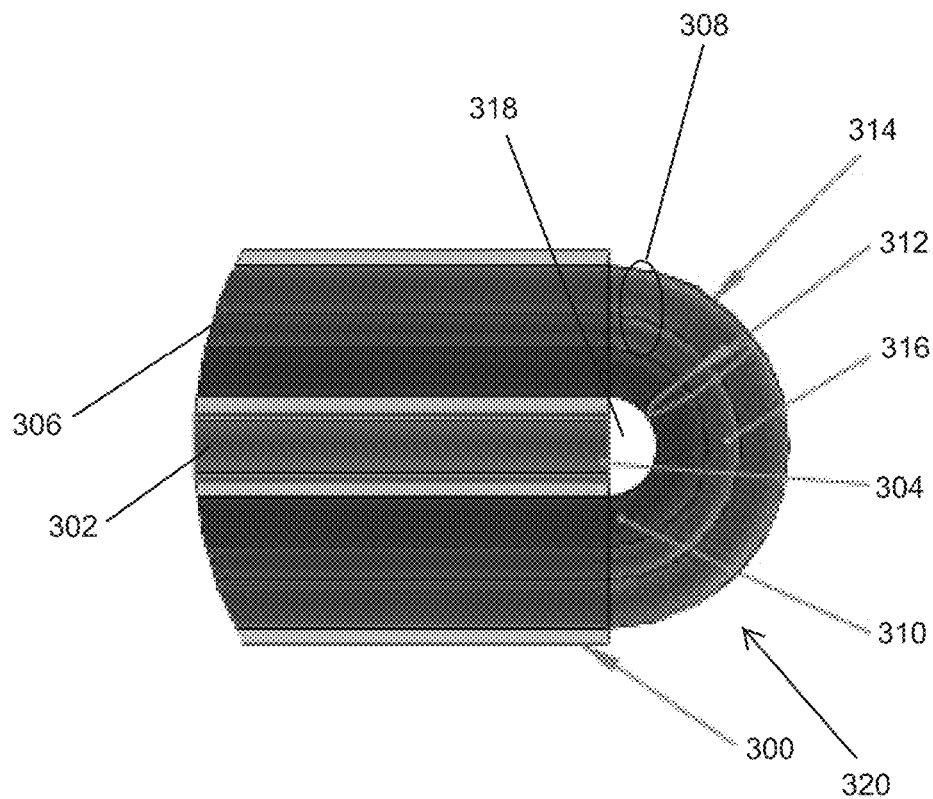
FIG. 8A depicts a side cross-sectional view of an epicardial implant catheter system according to embodiments.
Figure 8B:
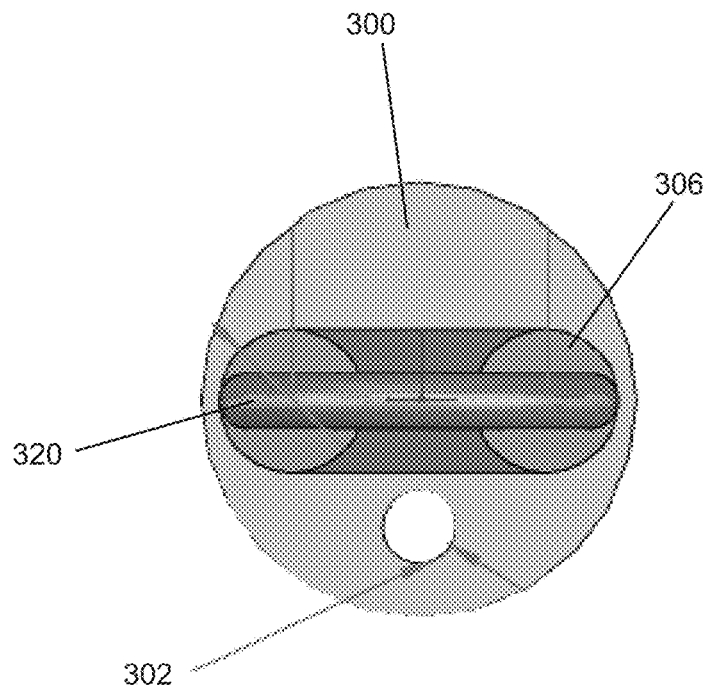
FIG. 8B depicts a front cross-sectional view of the epicardial implant catheter system of FIG. 8A according to embodiments.

FIGS. 8A-8H depict an embodiment of an implant delivery system in the form of a catheter system. Turning first to FIG. 8A, a cross-sectional view of the catheter system is shown. The catheter system may include a catheter body, such as advancing sheath 300 that defines at least one lumen. As shown here, sheath 300 defines three lumens. A first lumen 302 is provided that is configured to receive a guide wire 304. Two outer lumens 306 are provided that receive an implant 320 that includes a positioning device 308 and at least one cuff 310. The positioning device 308 may include a containment sheath 312, a support wire 314, and a shape memory wire 316. The containment sheath 312 may extend around the support wire 314, shape memory wire 316, and catheter with cuff 310. In some embodiments, the first lumen 302 may be offset from the two outer lumens 306 such that the positioning device is in a different plane than the guide wire 304 as shown in FIG. 8B.

Figure 8C:
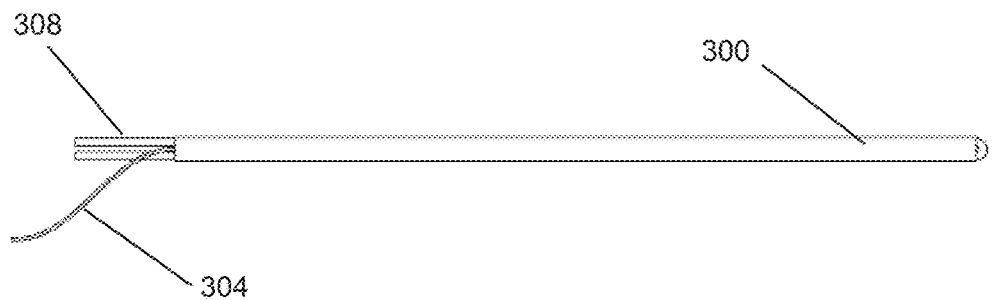
FIG. 8C depicts a top view of the epicardial implant catheter system of FIG. 8A according to embodiments.
Figure 8D:
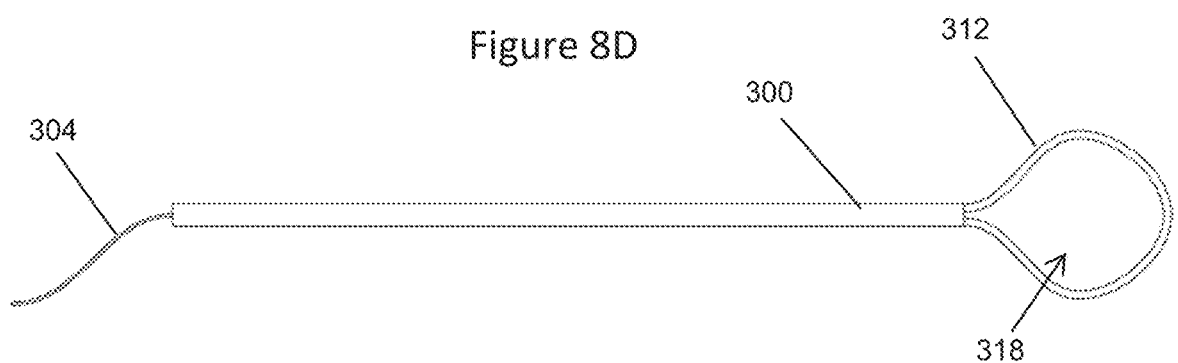
FIG. 8D depicts a top view of the epicardial implant catheter system of FIG. 8A with a positioning device in an advanced position according to embodiments.

The advancing sheath 300 may be elongated such that it constrains all or a substantial portion of the positioning device 308 and cuff 310 as shown in FIG. 8C. This elongate advancing sheath may be inserted percutaneously for placement of the positioning device 308 and cuff 310 around an atrial appendage. For example, the guide wire 304 may be inserted into the patient. The guide wire 304 is reciprocatably received within the catheter body 300 and is configured to manipulate a position of the positioning device 308, the advancing sheath 300, and cuff 310 to a proper location. When near the atrial appendage, the advancing sheath 300 may be at least partially retracted, exposing at least a portion of the positioning device 308 as shown in FIG. 8D. In some embodiments, the exposure of the positioning device 308 may be a result of the positioning device 308 being pushed out of the advancing sheath 300. This allows the support wire 314 to be unconstrained, enabling the support wire 314 to expand the positioning device 308. For example, the support wire 314 may be biased to expand to a circular, ovoid, and/or other generally open shape when unconstrained. This allows the positioning device 308 to include two sides and a distal end that define an open interior 318 in which the atrial appendage may be received. The size of the open interior 318 may be determined by how far the advancing sheath 300 is retracted, with a larger retraction resulting in a larger sized open interior 318. While shown here having a loop shape, it will be appreciated that the positioning device 308 and/or support wire 314 may have other shapes that define open interiors, such as hook shapes.

Figure 8E:
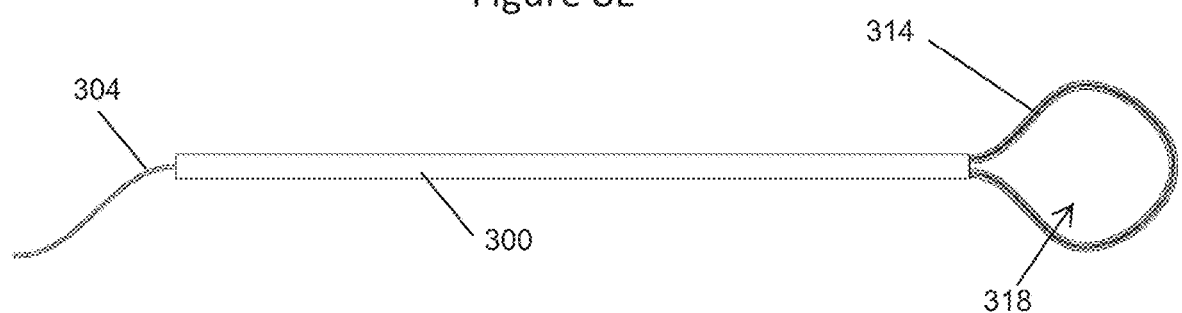
FIG. 8E depicts a top view of the epicardial implant catheter system of FIG. 8A with a containment sheath removed according to embodiments.

After advancing the positioning device 308, the containment sheath 312 may be removed, exposing the support wire 314, shape memory wire 316, and cuff 310 as shown in FIG. 8E. In some embodiments, the removal of the containment sheath 312 may be done once the shape memory wire 316 is set. This exposes the uninflated cuff 310 or balloon.

Figure 8F:
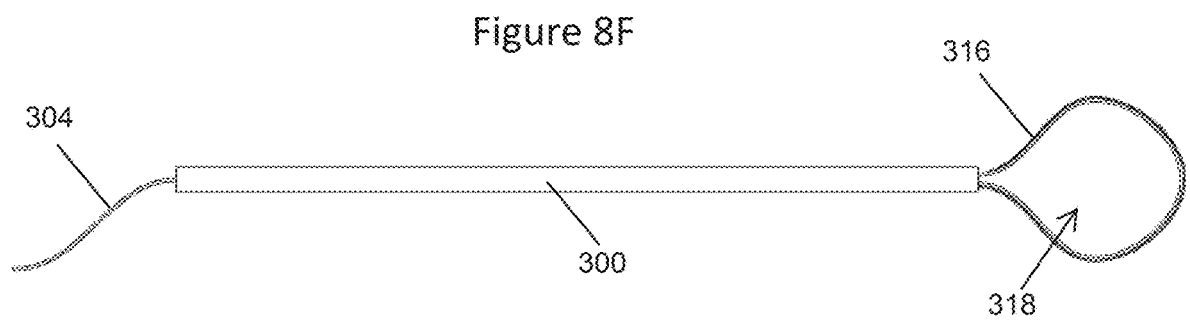
FIG. 8F depicts a top view of the epicardial implant catheter system of FIG. 8A with a support wire removed according to embodiments.
Figure 8G:
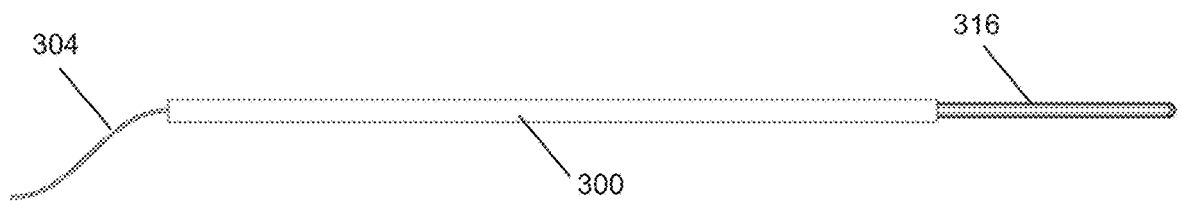
FIG. 8G depicts a top view of the epicardial implant catheter system of FIG. 8A with a shape memory wire in a memory shape position according to embodiments.

In some embodiments, the support wire 314 may be configured to restrict the shape memory wire 316 from retaining its preset shape. Once the open interior 318 is properly positioned around the atrial appendage, the support wire 314 may be removed from the catheter system as shown in FIG. 8F. This allows the shape memory wire 316 to return to its shape memory as shown in FIG. 8G. For example, the shape memory wire 316 may be formed of nitinol, or a similar shape memory material, and may be formed to contract into a more compact shape that may capture and/or compress the atrial appendage. In some embodiments, the shape memory wire 316 may grab the atrial appendage lightly so as to just maintain a position of the implant, while in other embodiments, the shape memory wire 316 is configured to firmly compress the appendage.

Figure 8H:
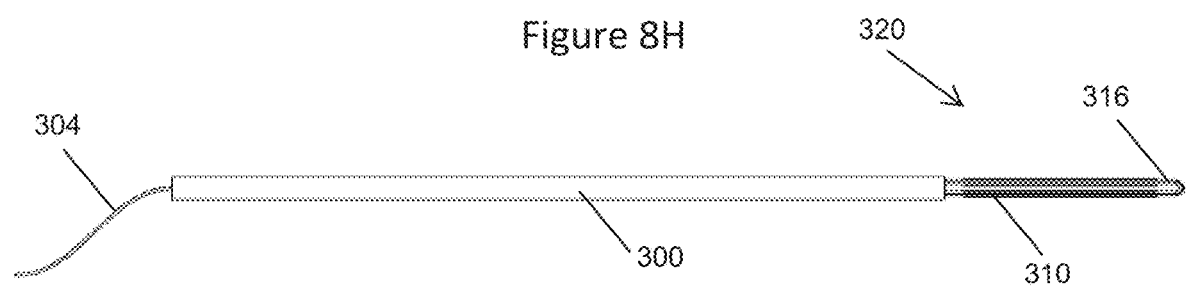
FIG. 8H depicts a top view of the epicardial implant catheter system of FIG. 8A with a cuff in an expanded state according to embodiments.

Upon removing the containment sheath 312, the cuff(s) 310 may be inflated and/or otherwise expanded into the open interior 318 as shown in FIG. 8H. The cuff(s) 310 may include a single cuff 310 or a series of cuffs 310 that are configured to contact multiple sides of the atrial appendage to occlude the appendage. In some embodiments, the cuff 310 may be generally u-shaped with a circular cross-section. For example, the u-shaped cuff 310 may include two sides and a distal end that defines the open interior 318. While shown having a round or circular cross-sectional shape, it will be appreciated that other cross-sectional and/or longitudinal shapes of cuffs 310 may be used. Additionally, rather than a single u-shaped cuff 310, a number of cuffs 310 may be provided to occlude the appendage. The cuff(s) 310 may be inflated by introducing a fluid into one or more reservoirs within each cuff 310. The fluid may be introduced gradually, which allows the implant 320 to be repositioned if necessary, without damaging the contacting heart tissue. In some embodiments, this may be achieved by introducing the fluid through a fluid supply tube (not shown). A one-way valve may be used to ensure that the fluid may not escape the cuff 310. In other embodiments, a clip or other clamping device may be secured around a portion of the fluid supply tube to cinch or squeeze the outer walls of the tube together, thereby sealing the interior of the tube. This allows the cuff 120 to be deflated again by removing the clip and allowing the fluid to escape the cuff 120. deflation of the cuff 120 may be necessary if the positioning device 104 moves out of a proper position.

Figure 8I:
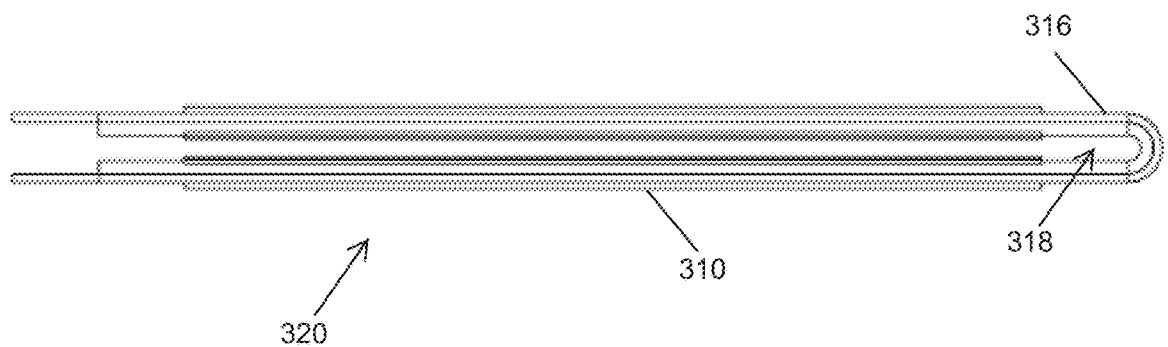
FIG. 8I depicts a top view of the epicardial implant catheter system of FIG. 8A with a positioning device and cuff in a detached state according to embodiments.

Once inflated the cuff(s) 310 squeeze and/or otherwise occlude the atrial appendage. Finally, after inflating the cuff(s) 310, the shape memory wire 316 and cuff(s) 310 are detached from the rest of the catheter system as shown in FIG. 8I. This allows the shape memory wire 316 and cuff(s) 310 to remain attached to the atrial appendage. To detach the cuff(s) 310, it may be necessary to clip or otherwise cut the fluid supply tube. This may be done at a position upstream of the one-way valve and/or clip to ensure that the cuff(s) 310 remains inflated. In some embodiments, a portion of the fluid supply tube may be burned off after the cuff(s) 310 have been inflated. This may serve to remove any excess tubing, as well as to melt the remaining tube shut to seal the cuff(s) 310.

In some embodiments, a grasping device such as that described in relation to FIG. 1 may be employed to grasp and releasably hold the atrial appendage to facilitate positioning and engagement of any of the implants 100, 200, and 320. Grasping device may typically comprise a conventional grasping tool, such as a suction tube which establishes negative pressure at a distal end thereof, the negative pressure being suitable to releasably retain tissue, such as the atrial appendage at distal end. Alternative grasping tools include thoracoscopic forceps and the like.

FIG. 9 depicts a process 900 for treating an atrial appendage using an epicardial implant. For example, process 900 may be performed using any of the epicardial implants described herein, such as implant 24, implant 100, implant 200, and implant 320. Process 900 may begin by providing the epicardial implant at block 902. The implant may include a positioning device and at least one expandable cuff that is expandable into at least a portion of the open interior of the positioning device. Access to the heart may be provided percutaneously, such as by using a catheter implant system such as implant 320 and/or during an open-chest procedure in which an implant system such as implant 24, 100, or 200 may be used. At block 904, the epicardial implant is positioned around an external surface of the atrial appendage such that a base of the atrial appendage is disposed in the open interior of the positioning device.

In percutaneous applications, the positioning device may include a support wire that is configured to expand the open interior of the positioning device for positioning about the base of the atrial appendage. The positioning device may also include a shape memory wire, such as a nitinol wire. To position the epicardial implant around an external surface of the atrial appendage, the support wire may be manipulated (using a guide wire) to a position in which an outer periphery of the support wire encircles at least a portion of the base of the atrial appendage. The support wire may then be removed, enabling the shape memory wire to rebound to a preset shape that is configured to close the open interior of the positioning device. that is guided around the base of the atrial appendage.

In open chest applications, the positioning device may be positioned around and closed about the atrial appendage using a forceps-like delivery device. The positioning device may be latched or otherwise secured about the appendage.

Once the implant has been properly positioned about the base of the atrial appendage, the at least one expandable cuff is expanded into the open interior of the positioning device to an extent sufficient to physically occlude the atrial appendage at the base at block 906. This may be done by introducing a fluid, such as saline, into an interior of the at least one expandable cuff via a fluid supply tube. For example, fluid may be introduced into the at least one expandable cuff via a one-way valve that interfaces with the fluid supply tube of the delivery device. In other embodiments, a clip or other clamping device may be secured around a portion of the fluid supply tube to cinch or squeeze the outer walls of the tube together, thereby sealing the interior of the tube.

In some embodiments, prior to expanding the at least one expandable cuff, the positioning device may be secured to the atrial appendage. This helps ensure that the implant does not move during the expansion step. The positioning device may be secured by tightening at least the first side and the second side of the positioning device such that the first side and the second side contact the atrial appendage. For example, in a percutaneous application, a shape memory wire may be used to clamp or otherwise close the positioning device against a surface of the atrial appendage.

Once the at least one expandable cuff has been expanded, the epicardial implant may be disengaged from a delivery device at block 908. For example, in a percutaneous application, a containment sheath, support wire, and advancing sheath may be retracted and the shape memory wire and cuff(s) may be cut or otherwise disengaged from the rest of the catheter system. As another example, in an open-heart application, a quick release mechanism may be actuated to release a handle of a delivery device from the positioning device and cuffs. Additionally, it may be necessary to clip or otherwise cut a fluid supply tube. This may be done at a position upstream of the one-way valve and/or clip to ensure that the cuffs remain inflated.

The invention has been described herein in considerable detail in order to comply with the patent statutes, and to provide those skilled in the art with the information needed to apply the novel principles and to construct and use embodiments of the invention as required. However, it is to be understood that the invention can be carried out by different methods/devices, and that various modifications can be accomplished without departing from the scope of the invention itself.

What is claimed is:

1. An epicardial implant, comprising:
a positioning device that defines an open interior, wherein:
the positioning device is configured to be detachably coupled with an implant delivery device such that the positioning device may be detached from the implant delivery device after the epicardial implant is in place about an atrial appendage; and
the positioning device comprises a first side, a second side, and a distal end that couples the first side and the second side;
at least one expandable cuff having a generally triangular cross-section, the at least one expandable cuff being coupled with the positioning device such that a flat surface of the at least one expandable cuff faces the open interior of the positioning device and a pointed surface of the at least one expandable cuff opposite the flat surface points away from the open interior of the positioning device, wherein:
the positioning device receives the at least one expandable cuff within a cuff housing that defines a recess that is shaped to receive the at least one expandable cuff when in an unexpanded state;
the positioning device is configured to selectively move the at least one expandable cuff toward and away from an atrial appendage to position the at least one expandable cuff in a desired position relative to the atrial appendage;

the at least one expandable cuff is expandable into at least a portion of the open interior of the positioning device following placement of the at least one expandable cuff into the desired position; and the at least one expandable cuff is configured to physically occlude a base of the atrial appendage when expanded.

2. The epicardial implant of claim 1, wherein:
the at least one expandable cuff comprises a balloon.

3. The epicardial implant of claim 1, wherein:
the distal end comprises a latch that is configured to releasably couple the first side and the second side.

4. The epicardial implant of claim 1, wherein:
the positioning device further comprises a hinged coupling between the first side and the second side such that the first side and the second side are movable relative to one another.

5. The epicardial implant of claim 1, wherein:
the positioning device is configured to house at least a portion of the at least one expandable cuff when the at least one expandable cuff is in an unexpanded state.

6. The epicardial implant of claim 1, wherein:
the at least one expandable cuff comprises a u-shaped balloon.

7. The epicardial implant of claim 1, wherein:
the positioning device comprises:
a support wire that is configured to expand the open interior for positioning about the base of the atrial appendage; and
a shape memory wire configured to close the open interior when the positioning device is properly positioned and the support wire is removed.

8. A catheter system, comprising:
a catheter body defining at least one lumen;
a positioning device disposed within the catheter body, the positioning device defining an open interior and comprising:
a support wire that is configured to expand the open interior for positioning about the base of the atrial appendage; and
a shape memory wire configured to close the open interior when the positioning device is properly positioned and the support wire is removed, wherein:
the positioning device is configured to extend from a distal end of the catheter body; and
the positioning device is configured to be positioned such that at least portion of a base of an atrial appendage is disposed within the open interior; and
at least one expandable cuff, wherein:
the positioning device is configured to selectively move the expandable cuff toward and away from the atrial appendage to position the at least one expandable cuff in a desired position relative to the atrial appendage;
the at least one expandable cuff is expandable into at least a portion of the open interior of the positioning device following placement of the at least one expandable cuff into the desired position; and
the at least one expandable cuff is configured to physically occlude a base of the atrial appendage when expanded.

9. The catheter system of claim 8, wherein:
the positioning device comprises one or more of a hook or a loop.

10. The catheter system of claim 8, wherein:
the shape memory wire comprises nitinol.

11. The catheter system of claim 8, further comprising:
a guide wire that is reciprocatably received within the catheter body and is configured to manipulate a position of the positioning device.

12. The catheter system of claim 8, wherein:
the at least one expandable cuff comprises a balloon having a first side, a second side, and a distal end.

13. A method for treating an atrial appendage, the method comprising:
providing an epicardial implant, the epicardial implant comprising:
a positioning device defining an open interior, wherein the positioning device comprises:
a first side, a second side, and a distal end that couples the first side and the second side;
a support wire that is configured to expand the open interior for positioning about the base of the atrial appendage; and
a shape memory wire; and
at least one expandable cuff that is expandable into at least a portion of the open interior of the positioning device;
positioning the epicardial implant around an external surface of the atrial appendage such that a base of the atrial appendage is disposed in the open interior of the positioning device by:
manipulating the support wire to a position in which an outer periphery of the support wire encircles at least a portion of the base of the atrial appendage; and
removing the support wire, thereby enabling the shape memory wire to rebound to a preset shape that is configured to close the open interior of the positioning device; and
expanding the at least one expandable cuff into the open interior of the positioning device to an extent sufficient to physically occlude the atrial appendage at the base.

14. The method for treating an atrial appendage of claim 13, further comprising:
securing the positioning device to the atrial appendage prior to expanding the at least one expandable cuff.

15. The method for treating an atrial appendage of claim 14, wherein:
securing the positioning device comprises tightening at least the first side and the second side of the positioning device such that the first side and the second side contact the atrial appendage.

16. The method for treating an atrial appendage of claim 13, further comprising:
upon expanding the at least one expandable cuff, disengaging the epicardial implant from a delivery device.

17. The method for treating an atrial appendage of claim 13, wherein:
expanding the at least one expandable cuff comprises introducing a fluid into an interior of the at least one expandable cuff via a fluid supply tube.

18. The method for treating an atrial appendage of claim 17, wherein:
the fluid is introduced into the at least one expandable cuff via a one-way valve that interfaces with the fluid supply tube.

* * * * *